(12) United States Patent
Nemes

(10) Patent No.: US 8,951,396 B2
(45) Date of Patent: Feb. 10, 2015

(54) CATHODIC MATERIALS FOR USE IN ELECTROCHEMICAL SENSORS AND ASSOCIATED DEVICES AND METHODS OF MANUFACTURING THE SAME

(71) Applicant: Gentex Corporation, Zeeland, MI (US)

(72) Inventor: Joel C. Nemes, Holland, MI (US)

(73) Assignee: Gentex Corporation, Zeeland, MI (US)

( * ) Notice: Subject to any disclaimer, the term of this patent is extended or adjusted under 35 U.S.C. 154(b) by 0 days.

(21) Appl. No.: 14/278,830

(22) Filed: May 15, 2014

(65) Prior Publication Data

US 2014/0246316 A1 Sep. 4, 2014

Related U.S. Application Data

(63) Continuation of application No. 14/148,211, filed on Jan. 6, 2014, which is a continuation of application No. 12/804,977, filed on Aug. 3, 2010, now Pat. No. 8,641,878.

(60) Provisional application No. 61/231,229, filed on Aug. 4, 2009.

(51) Int. Cl.
*G01N 27/407* (2006.01)
*G01N 27/404* (2006.01)
*G01N 33/00* (2006.01)
(Continued)

(52) U.S. Cl.
CPC ........ *G01N 27/4075* (2013.01); *G01N 27/4045* (2013.01); *G01N 33/004* (2013.01); *H01M 4/9008* (2013.01); *H01M 4/9083* (2013.01); *G01N 27/407* (2013.01); *H01M 8/1004* (2013.01); *H01M 2008/1095* (2013.01); *Y02E 60/50* (2013.01)
USPC ............ 204/433; 204/418; 204/424; 204/426

(58) Field of Classification Search
USPC ........................ 204/400–435; 205/775–794.5
See application file for complete search history.

(56) References Cited

U.S. PATENT DOCUMENTS

| 4,329,214 A | 5/1982 | Spritzer et al. |
| 5,164,053 A | 11/1992 | Razaq et al. |

(Continued)

FOREIGN PATENT DOCUMENTS

| EP | 1 553 052 | 7/2005 |
| JP | 2003-515131 | 4/2003 |

(Continued)

OTHER PUBLICATIONS

Non-Final Office Action in U.S. Appl. No. 14/148,211 dtd Jun. 24, 2014 (17 pages).

(Continued)

*Primary Examiner* — Susan D Leong
(74) *Attorney, Agent, or Firm* — Foley & Lardner LLP; Scott P. Ryan

(57) ABSTRACT

A cathodic material for use in an electrochemical sensor comprising: a carbonaceous material and an oxygen reduction catalyst associated with the carbonaceous material; and wherein the cathodic material does not materially exhibit catalytic activity for the oxidation of carbon monoxide. Associated electrochemical sensors may include an anode and cathode that are disposed upon the same or opposite sides of an ion exchange membrane and/or exposed to the same or different gaseous environments.

18 Claims, 13 Drawing Sheets

(51) Int. Cl.
*H01M 4/90* (2006.01)
*H01M 8/10* (2006.01)

(56) References Cited

U.S. PATENT DOCUMENTS

| | | |
|---|---|---|
| 5,211,984 A | 5/1993 | Wilson |
| 5,280,115 A | 1/1994 | Ellis et al. |
| 5,302,274 A | 4/1994 | Tomantschger et al. |
| 5,331,310 A | 7/1994 | Stetter et al. |
| 5,573,648 A | 11/1996 | Shen et al. |
| 5,605,664 A | 2/1997 | Lauks et al. |
| 5,618,493 A | 4/1997 | Goldstein et al. |
| 5,650,054 A | 7/1997 | Shen et al. |
| 5,944,969 A | 8/1999 | Scheffler et al. |
| 5,958,200 A | 9/1999 | Kessel |
| 6,172,759 B1 | 1/2001 | Goldstein |
| 6,200,443 B1 | 3/2001 | Shen et al. |
| 6,454,923 B1 | 9/2002 | Dodgson et al. |
| 6,800,391 B2 | 10/2004 | Odgaard et al. |
| 6,936,147 B2 | 8/2005 | Prohaska et al. |
| 6,948,352 B2 | 9/2005 | Rabbett et al. |
| 7,022,213 B1 | 4/2006 | Austen et al. |
| 7,077,938 B1 | 7/2006 | Austen et al. |
| 7,236,095 B2 | 6/2007 | Smith et al. |
| 7,279,081 B2 | 10/2007 | Maeno et al. |
| 2002/0076583 A1 | 6/2002 | Reiser et al. |
| 2003/0145644 A1 | 8/2003 | Rabbett et al. |
| 2004/0028976 A1 | 2/2004 | Cabasso et al. |
| 2004/0137310 A1 | 7/2004 | Kiros |
| 2004/0236157 A1 | 11/2004 | Heilgendorff et al. |
| 2005/0095698 A1 | 5/2005 | Carlson |
| 2005/0145494 A1 | 7/2005 | Inoue et al. |
| 2006/0091007 A1 | 5/2006 | Inoue et al. |
| 2006/0120924 A1 | 6/2006 | Inoue et al. |
| 2006/0151332 A1 | 7/2006 | Stull et al. |
| 2006/0196770 A1 | 9/2006 | Tomohiro et al. |
| 2007/0196722 A1 | 8/2007 | Tomita et al. |
| 2007/0248752 A1 | 10/2007 | O'Brien et al. |
| 2008/0161183 A1 | 7/2008 | Popov et al. |
| 2008/0286490 A1 | 11/2008 | Bogdanoff et al. |

FOREIGN PATENT DOCUMENTS

| | | |
|---|---|---|
| JP | 2004-170101 | 6/2004 |
| JP | 2004-226346 | 8/2004 |
| JP | 2006-331689 | 12/2006 |
| WO | WO 01/36956 | 5/2001 |
| WO | WO-2008/094222 | 8/2008 |

OTHER PUBLICATIONS

Official Action in Japanese Application No. 2012-523603 dtd May 14, 2014 (English summary included—3 pages).

International Search Report and Written Opinion of the International Searching Authority issued in PCT/US2010/002156 dtd Oct. 14, 2010.

First Office Action issued in Canadian Application No. 2,770,150 dtd Sep. 10, 2013 (3 pages).

First Office Action issued in Chinese Application No. 201080041964.0 dtd Jan. 6, 2014 (English translation—3 pages).

Krasnikov, et al., "Electronic structure of Ni(II) porphyrins and phthalocyanine studied soft X-ray absorption spectroscopy," Chemical Physics 332, 2007, pp. 318-324.

Nakamura, et al., "Plasma polymerization of cobalt tetraphenylporphyrin and the functionalities of the thin films produced," Thin Solid Films 345, 1999, pp. 99-103.

Office Action in Japanese Application No. 2012-523603 dtd May 1, 2013 (7 pages—English translation included).

Somashekarappa, et al., "Self-assembled molecular films of tetraamino metal (Co, cu, Fe) phthalocyanines on gold and silver. Electrochemical and spectroscopic characterization," Pure and Applied chemistry, vol. 74, No. 9, 2002, pp. 1609-1620.

Vincent, et al., "Electrocatalytic hydrogen oxidation by an enzyme at high carbon monoxide or oxygen levels," Proceedings of the National Academy of Sciences [online], Nov. 22, 2005 [retrieved on Sep. 27, 2010], vol. 102, No. 47, pp. 16951-16954.

Zagal, et al., "Linear versus volcano correlations between electrocatalytic activity and redox and electronic properties of metallophthalocyanines," Electrochimica Acta 44, 1998, pp. 1349-1357.

Final Office Action in U.S. Appl. No. 12/804,977 dtd Nov. 2, 2012 (33 pages).

Non-Final Office Action in U.S. Appl. No. 12/804,977 dtd Mar. 28, 2013 (23 pages).

Non-Final Office Action in U.S. Appl. No. 12/804,977 dtd Apr. 12, 2012 (20 pages).

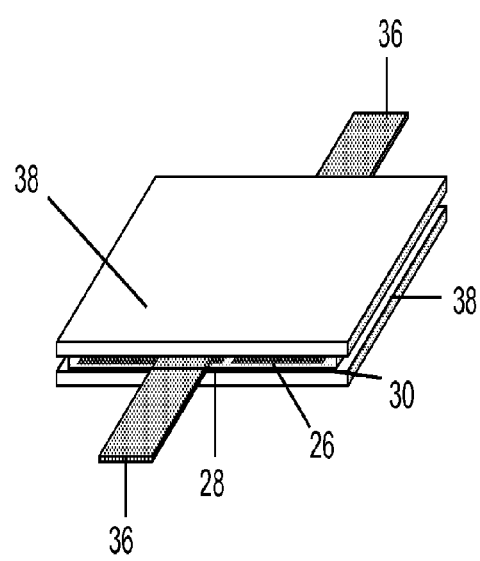
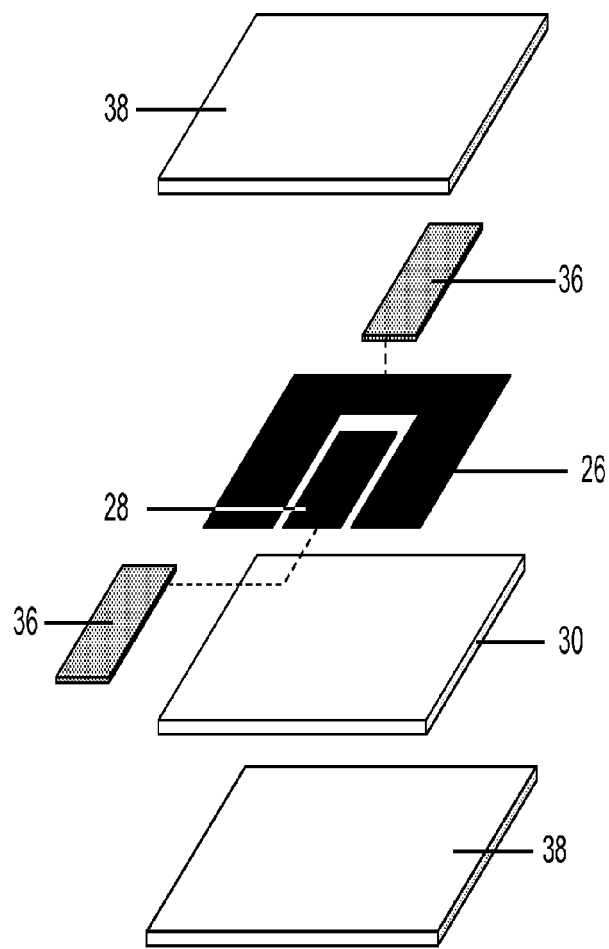
Figure 2A
Figure 2B

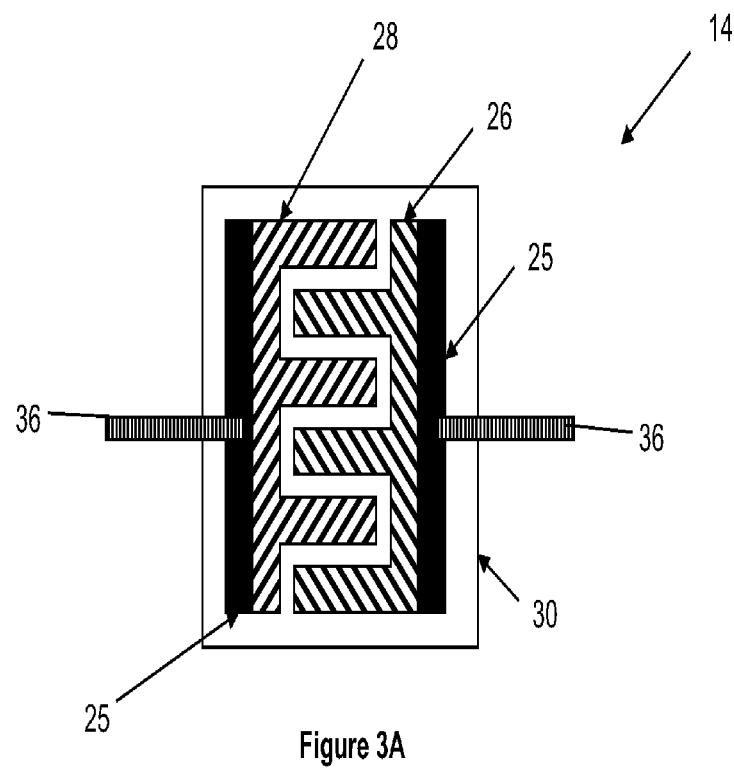
Figure 3A
Alternative Patterns
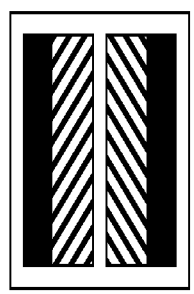 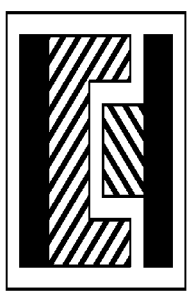 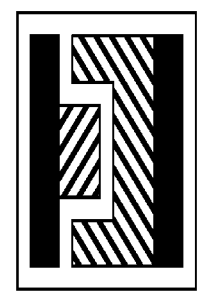
Figure 3B　　Figure 3C　　Figure 3D

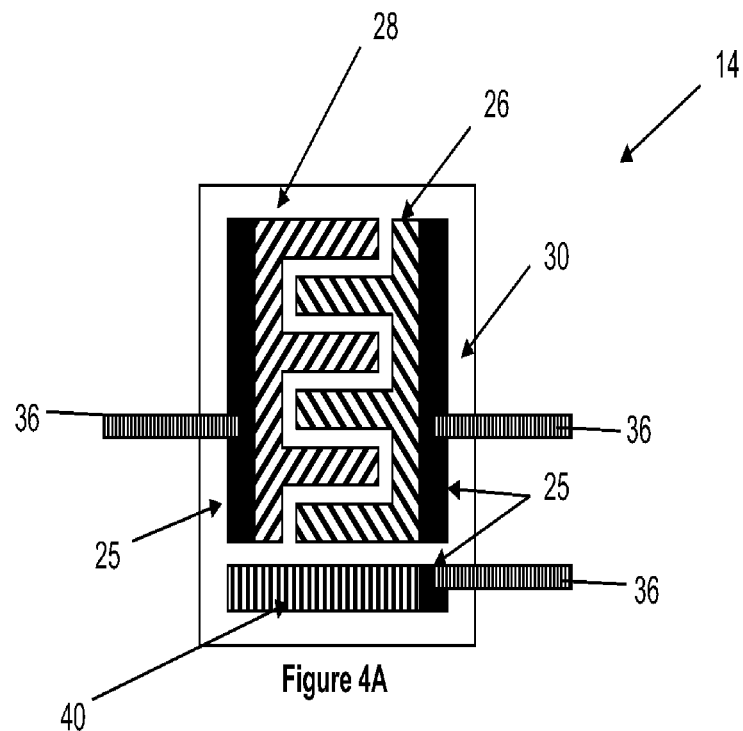
Figure 4A
Alternative Patterns
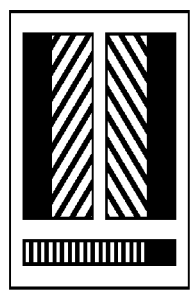 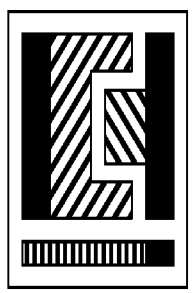 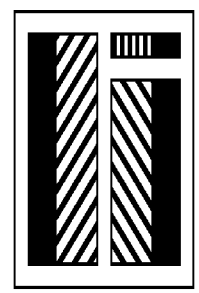
Figure 4B   Figure 4C   Figure 4D Figure 9a. Operation of Sensor 1 under 390±10 ppm pulses of CO Figure 9b. Operation of Sensor 2 under 390±10 ppm pulses of CO Linear Response of CO Sensor from 30-400 ppm CO at 45% RH 1. Anode
2. Cathode
3. Ion Exchange Membrane
4. Sensing Circuit Prior Art Micro Electrode Assembly

CATHODIC MATERIALS FOR USE IN ELECTROCHEMICAL SENSORS AND ASSOCIATED DEVICES AND METHODS OF MANUFACTURING THE SAME

CROSS-REFERENCE TO RELATED APPLICATION(S)

This application is a continuation of U.S. patent application Ser. No. 14/148,211, filed on Jan. 6, 2014, which in turn is a continuation of U.S. application Ser. No. 12/804,977, filed Aug. 3, 2010, now U.S. Pat. No. 8,641,878, issued Feb. 4, 2014, entitled "Cathodic Materials For Use In Electrochemical Sensors And Associated Devices And Methods Of Manufacturing The Same," which claims the benefit of U.S. Provisional Application Ser. No. 61/231,229, filed Aug. 4, 2009, entitled "Cathodic Materials For Use In Electrochemical Sensors And Associated Devices," which are hereby incorporated herein by reference in their entirety, including all references cited therein.

BACKGROUND OF THE INVENTION

1. Field of the Invention

The present invention relates in general to cathodic materials for use in fuel cells and electrochemical sensors and, more particularly, to carbonaceous materials associated with oxygen reduction catalysts, for example, substituted and unsubstituted transition metal porphyrins, substituted and unsubstituted transition metal tetrabenzoporphyrins, substituted and unsubstituted transition metal tetraphenylporphyrins, substituted and unsubstituted transition metal tetraazaporphyrins, substituted and unsubstituted transition metal tetraazamacrocycles, substituted and unsubstituted transition metal phthalocyanines, substituted and unsubstituted transition metal naphthalocyanines, substituted and unsubstituted transition metal bis(phthalocyanines), substituted and unsubstituted transition metal bis(naphthalocyanines), and combinations thereof. The present invention further relates to fuel cells and electrochemical sensors having novel structural configurations, wherein the anode and the cathode of an associated micro electrode assembly (MEA) are disposed upon the same side or different sides of an ion exchange membrane, and/or exposed to the same gaseous environment or different gaseous environments—among other configurations. The present invention also relates to gas, smoke and/or fire detectors comprising novel electrochemical sensors, micro electrode assemblies, and/or sub-components for the same, as well as associated methods of manufacturing.

2. Background Art

Fuel cells and electrochemical sensors for use in, for example, gas, smoke, and/or fire detectors have been known in the art for several years. See, for example, U.S. Pat. No. 4,329,214 entitled "Gas Detection Unit," U.S. Pat. No. 5,302,274 entitled "Electrochemical Gas Sensor Cells Using Three Dimensional Sensing Electrodes," U.S. Pat. No. 5,331,310 entitled "Amperometric Carbon Monoxide Sensor Module for Residential Alarms," U.S. Pat. No. 5,573,648 entitled "Gas Sensor Based on Protonic Conductive Membranes," U.S. Pat. No. 5,618,493 entitled "Photon Absorbing Bio-derived Organometallic Carbon Monoxide Sensors," U.S. Pat. No. 5,650,054 entitled "Low Cost Room Temperature Electrochemical Carbon Monoxide and Toxic Gas Sensor with Humidity Compensation Based on Protonic Conductive Membranes," U.S. Pat. No. 5,944,969 entitled "Electrochemical Sensor With A Non-Aqueous Electrolyte System," U.S. Pat. No. 5,958,200 entitled "Electrochemical Gas Sensor," U.S. Pat. No. 6,172,759 entitled "Target Gas Detection System with Rapidly Regenerating Optically Responding Sensors," U.S. Pat. No. 6,200,443 entitled "Gas Sensor with a Diagnostic Device," U.S. Pat. No. 6,936,147 entitled "Hybrid Film Type Sensor," U.S. Pat. No. 6,948,352 entitled "Self-Calibrating Carbon Monoxide Detector and Method," U.S. Pat. No. 7,077,938 entitled "Electrochemical Gas Sensor," U.S. Pat. No. 7,022,213 entitled "Gas Sensor and Its Method of Manufacture," U.S. Pat. No. 7,236,095 entitled "Solid State Sensor for Carbon Monoxide," U.S. Pat. No. 7,279,081 entitled "Electrochemical Sensor," U.S. Patent Publication No. 2005/0145494 entitled "Liquid Electrochemical Gas Sensor," U.S. Patent Publication No. 2006/0091007 entitled "Gas Detecting Device with Self-Diagnosis for Electrochemical Gas Sensor," U.S. Patent Publication No. 2006/0120924 entitled "Proton Conductor Gas Sensor," and U.S. Patent Publication No. 2006/0196770 entitled "Liquid Electrochemical Gas Sensor," all of which are hereby incorporated herein by reference in their entirety—including all references cited therein.

While the utilization of fuel cells and electrochemical sensors for use in gas, smoke, and/or fire detectors has become increasingly popular, sensor performance, cost, longevity, and/or configuration remains largely problematic.

Indeed, modern fuel cells and electrochemical sensors commonly use carbon supported noble metal catalysts, such as platinum at both the anode and the cathode. At the anode, platinum typically catalyses the oxidation of the fuel, such as hydrogen, methanol, carbon monoxide, etcetera. At the cathode, platinum typically catalyses the reduction of oxygen. For example, the chemical reactions that typically occur in an electrochemical carbon monoxide sensor are provided below:

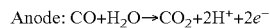

Anode: $CO + H_2O \rightarrow CO_2 + 2H^+ + 2e^-$

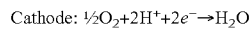

Cathode: $\frac{1}{2}O_2 + 2H^+ + 2e^- \rightarrow H_2O$

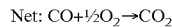

Net: $CO + \frac{1}{2}O_2 \rightarrow CO_2$

As is shown in FIG. 10, due to the identical nature of the catalyst electrodes, without biasing the electrodes, electric current generation ($e^-$) can typically only occur if both the anode and the cathode are separated and sealed from each other to prevent gas crossover. The two electrodes are typically separated by a membrane that allows for diffusion of ions, such as protons ($H^+$), and water ($H_2O$). Gas crossover through the membrane is possible, but the diffusion rate of the sample gas is controlled so that the fuel gas ($H_2$, CO, etcetera) is effectively scrubbed from the sample gas by the anode and only oxygen is allowed to crossover to the cathode.

When both the anode and the cathode comprise identical materials, in this case carbon supported platinum, there can be several problems. The first occurs when the gas diffusion is not controlled and the gases crossover from one electrode to the other. This can lead to degradation of the electrodes through peroxide formation or oxidation. In an electrochemical sensor, gas crossover results in reduced signal strength and polarization of the sensor which can potentially lead to sensor malfunction. Platinum is sensitive to poisoning from external contaminants, such as sulfur compounds, which reduces the electrical current being generated. Electrode sensitivity can also drop over time due to reduced surface area of the platinum particles caused by rearrangement and sintering. Additionally, amorphous carbon which is a common material used as a carbon support, (e.g., XC72 (Cabot Corporation) or Black Pearls (Cabot Corporation)) is susceptible to oxidation. The oxidation reaction can even be catalyzed by the very materials that the carbon is meant to support, such as Pt, Ru, Pd, etcetera. This oxidation can result in the presence of a background current in a sensor application, reduced electrical conductivity within the electrodes, and migration and aggregation of metal nanoparticles resulting in reduced power output or sensitivity. This is especially problematic for a sensor application in which long term drift and reduced sensitivity can be catastrophic. Finally, platinum is a noble metal that is rare and expensive.

It is therefore an object of the present invention, among other objects, to provide novel anodic and/or cathodic materials which replace conventional platinum based electrodes in fuel cells and electrochemical sensors. It is also an object of the present invention to provide novel device configurations which are enabled by the use of these novel materials for the anode and/or cathode.

These and other objects of the present invention will become apparent in light of the present specification, claims, and drawings.

SUMMARY OF THE INVENTION

The present invention is directed to a cathodic material for use in an electrochemical sensor comprising: a carbonaceous material and an oxygen reduction catalyst associated with the carbonaceous material, wherein the cathodic material does not materially exhibit catalytic activity for the oxidation of carbon monoxide. The carbonaceous material preferably acts as a support and/or an electron conductor. The cathodic material is also optionally associated with an ion-exchange material, such as proton conducting Nafion (Dupont), polystyrene sulfonic acid (Sigma-Aldrich), $H_3PO_4$ doped polybenzimidazole derivatives (L. Xiao, et al., *Fuel Cells* 5 (2005) 287), protic ionic liquid doped polybenzimidazole derivatives, and protic ionic liquid doped sulfonated polyimide derivatives (S.-Y. Lee, et al., *J. Power Sources* (2009)), etcetera.

In a preferred embodiment of the present invention, the oxygen reduction catalyst comprises a material resulting from pyrolysis of at least one of the group comprising substituted transition metal (i.e., d-block) porphyrins, unsubstituted transition metal porphyrins, substituted transition metal tetrabenzoporphyrins, unsubstituted transition metal tetrabenzoporphyrins, substituted transition metal tetraphenylporphyrins, unsubstituted transition metal tetraphenylporphyrins, substituted transition metal tetraazaporphyrins, unsubstituted transition metal tetraazaporphyrins, substituted transition metal tetraazamacrocycles, unsubstituted transition metal tetraazamacrocycles, substituted transition metal phthalocyanines, unsubstituted transition metal phthalocyanines, substituted transition metal naphthalocyanines, unsubstituted transition metal naphthalocyanines, substituted transition metal bis(phthalocyanines), unsubstituted transition metal bis(phthalocyanines), substituted transition metal bis(naphthalocyanines), unsubstituted transition metal bis(naphthalocyanines), and/or combinations thereof.

In another preferred embodiment of the present invention, the oxygen reduction catalyst comprises a material resulting from pyrolysis of at least one of the group comprising substituted cobalt porphyrins, unsubstituted cobalt porphyrins, substituted cobalt tetrabenzoporphyrins, unsubstituted cobalt tetrabenzoporphyrins, substituted cobalt tetraphenylporphyrins, unsubstituted cobalt tetraphenylporphyrins, substituted cobalt tetraazaporphyrins, unsubstituted cobalt tetraazaporphyrins, substituted cobalt tetraazamacrocycles, unsubstituted cobalt tetraazamacrocycles, substituted cobalt metal phthalocyanines, unsubstituted cobalt phthalocyanines, substituted cobalt naphthalocyanines, unsubstituted cobalt naphthalocyanines, substituted cobalt bis(phthalocyanines), unsubstituted cobalt bis(phthalocyanines), substituted cobalt bis(naphthalocyanines), unsubstituted cobalt bis(naphthalocyanines), and/or combinations thereof.

In yet another preferred embodiment of the present invention, the oxygen reduction catalyst comprises a material resulting from pyrolysis of at least one of a compound, a structural isomer of a compound, and mixtures of isomers of compounds, represented by the following structure:

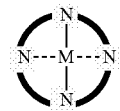

(I)

wherein M comprises a transition metal ligated by a tetraazamacrocycle, including, but not limited to, substituted porphyrins, unsubstituted porphyrins, substituted phthalocyanines, unsubstituted phthalocyanines, substituted naphthalocyanines, unsubstituted naphthalocyanines, and combinations thereof—just to name a few.

In one embodiment of the present invention, the oxygen reduction catalyst comprises a material resulting from pyrolysis of at least one of a compound, a structural isomer of a compound, and mixtures of isomers of compounds, represented by the following formula:

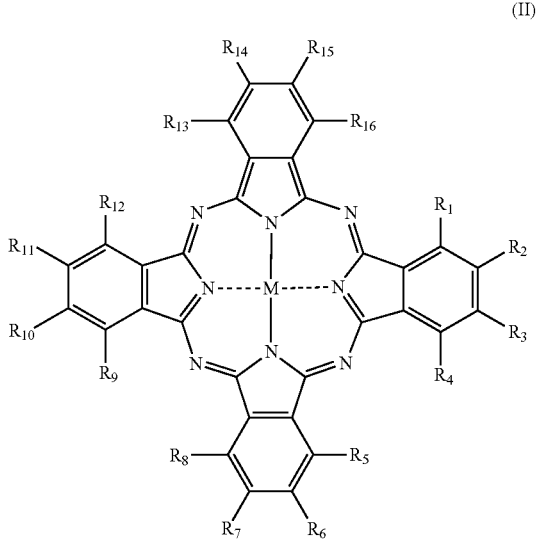

(II)

wherein M comprises Co, Cu, Fe, Ir, Ni, Pd, Rh, Ru, or Zn; wherein $R_1$-$R_{16}$ are the same or different and comprise H, $NO_2$, $NH_2$, $NHR_{17}$, $N(R_{18})_2$, $CO_2H$, $CO_2R_{19}$, an alkyl group containing approximately 1 to approximately 10 carbon atom(s), $OR_{20}$, SH, $SR_{21}$, and combinations thereof; and wherein $R_{17-21}$ are the same or different and comprise an alkyl group containing approximately 1 to approximately 10 carbon atom(s). In this embodiment, the oxygen reduction catalyst preferably comprises a material resulting from pyrolysis of one or more of a compound, a structural isomer of a compound, and mixtures of isomers of compounds, represented by the following formulae:

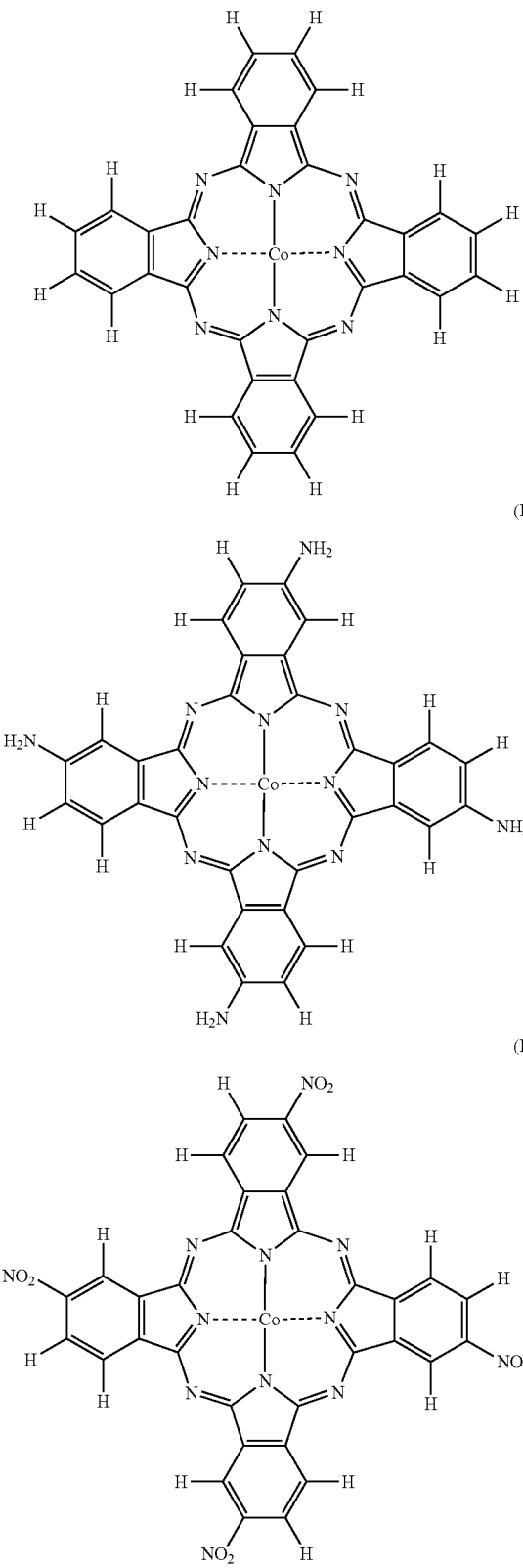

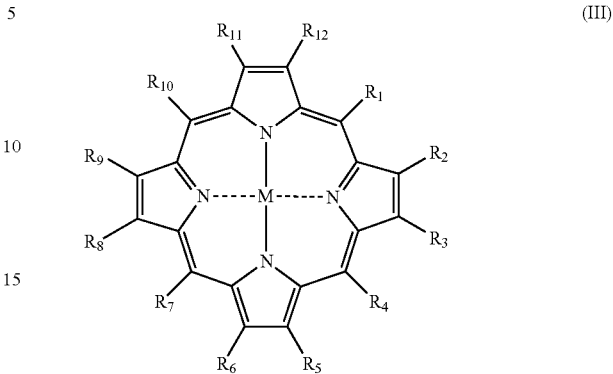

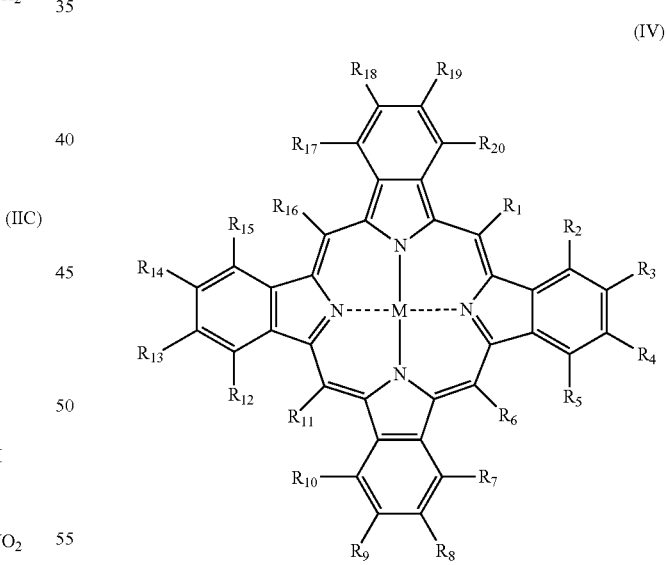

In a preferred embodiment of the present invention, the oxygen reduction catalyst comprises a material resulting from pyrolysis of at least one of a compound, a structural isomer of a compound, and mixtures of isomers of compounds, represented by the following formula:

wherein M comprises Co, Cu, Fe, Ir, Ni, Pd, Rh, Ru, or Zn; wherein $R_1$-$R_{12}$ are the same or different and comprise H, $NO_2$, $NH_2$, $NHR_{13}$, $N(R_{14})_2$, $CO_2H$, $CO_2R_{15}$, an alkyl group containing approximately 1 to approximately 10 carbon atom(s), $OR_{16}$, SH, $SR_{17}$, and combinations thereof; and wherein $R_{13-17}$ are the same or different and comprise an alkyl group containing approximately 1 to approximately 10 carbon atom(s).

In another preferred embodiment of the present invention, the oxygen reduction catalyst comprises a material resulting from pyrolysis of at least one of a compound, a structural isomer of a compound, and mixtures of isomers of compounds, represented by the following formula:

wherein M comprises Co, Cu, Fe, Ir, Ni, Pd, Rh, Ru, or Zn; wherein $R_1$-$R_{20}$ are the same or different and comprise H, $NO_2$, $NH_2$, $NHR_{21}$, $N(R_{22})_2$, $CO_2H$, $CO_2R_{23}$, an alkyl group containing approximately 1 to approximately 10 carbon atom(s), $OR_{24}$, SH, $SR_{25}$, and combinations thereof; and wherein $R_{21-25}$ are the same or different and comprise an alkyl group containing approximately 1 to approximately 10 carbon atom(s).

In yet another preferred embodiment of the present invention, the oxygen reduction catalyst comprises a material resulting from pyrolysis of at least one of a compound, a structural isomer of a compound, and mixtures of isomers of compounds, represented by the following formula:

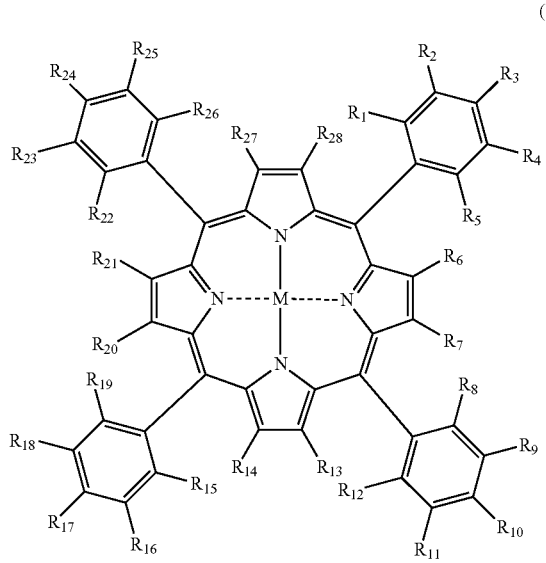

(V)

wherein M comprises Co, Cu, Fe, Ir, Ni, Pd, Rh, Ru, or Zn; wherein $R_1$-$R_{28}$ are the same or different and comprise H, $NO_2$, $NH_2$, $NHR_{29}$, $N(R_{30})_2$, $CO_2H$, $CO_2R_{31}$, an alkyl group containing approximately 1 to approximately 10 carbon atom(s), $OR_{32}$, SH, $SR_{33}$, and combinations thereof; and wherein $R_{29-33}$ are the same or different and comprise an alkyl group containing approximately 1 to approximately 10 carbon atom(s).

In one aspect of an embodiment of the present invention, the oxygen reduction catalyst comprises a material resulting from pyrolysis of at least one of a compound, a structural isomer of a compound, and mixtures of isomers of compounds, represented by the following formula:

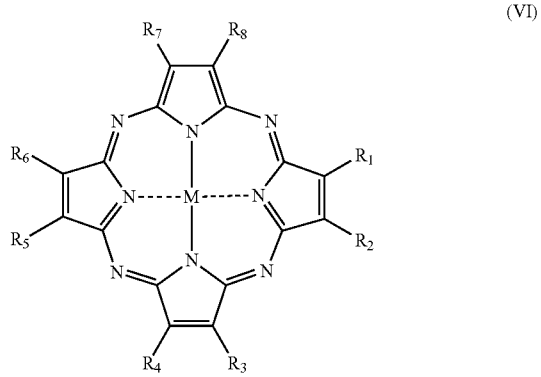

(VI)

wherein M comprises Co, Cu, Fe, Ir, Ni, Pd, Rh, Ru, or Zn; wherein $R_1$-$R_8$ are the same or different and comprise H, $NO_2$, $NH_2$, $NHR_9$, $N(R_{10})_2$, $CO_2H$, $CO_2R_{11}$, an alkyl group containing approximately 1 to approximately 10 carbon atom(s), $OR_{12}$, SH, $SR_{13}$, and combinations thereof; and wherein $R_{9-13}$ are the same or different and comprise an alkyl group containing approximately 1 to approximately 10 carbon atom(s).

Preferably, the carbonaceous materials associated with the present invention comprise, for example, graphene, graphite, amorphous carbon, carbon nanotubes, carbon fibers, and combinations thereof. The carbon nanotubes include, for example, single walled nanotubes (SWNT), double walled nanotubes (DWNT), and multi-walled nanotubes (MWNT), all of which may optionally be doped with atoms such as, but not limited to, nitrogen, boron, and/or phosphorous.

The present invention is also directed to an electrochemical sensor for use in a gas detector comprising: a housing, wherein the housing is capable of containing a micro electrode assembly therein (e.g., one or more side walls, and a bottom wall cooperatively define a containment region for containing the micro electrode assembly), and further wherein the housing comprises a gaseous diffusion aperture; and a micro electrode assembly which comprises an anode, a cathode comprising one or more cathodic materials as are disclosed herein, and an ion exchange membrane, wherein the ion exchange membrane permits ion transport (e.g., hydrogen ions (protons), hydroxide ions, carbonate ions, etcetera) between the anode and the cathode, and further wherein the ion exchange membrane prevents electron conduction between the anode and the cathode. The electrochemical sensor may also include a desiccant for retaining a liquid, such as water and/or a reservoir. The electrochemical sensor may further comprise a configuration to prevent water from freezing, such as antifreeze or salts. The electrochemical sensor may additionally comprise a configuration that is at least substantially waterless (See FIG. 1B).

In a preferred embodiment of the present invention, the anode and the cathode of the micro electrode assembly are disposed upon opposite sides of the ion exchange membrane and/or exposed to a different gaseous environment (e.g., a first configuration). Alternatively, the anode and the cathode of the micro electrode assembly are disposed upon the same side of the ion exchange membrane and/or exposed to the same gaseous environment (e.g., a second configuration).

The present invention is further directed to an electrochemical sensor for use in a gas detector comprising: a housing, wherein the housing is capable of containing a micro electrode assembly therein (e.g., one or more side walls, and a bottom wall cooperatively define a containment region for containing the micro electrode assembly), and further wherein the housing comprises a gaseous diffusion aperture; and a micro electrode assembly which comprises an anode, a cathode, and an ion exchange membrane, wherein the anode and the cathode are disposed upon the same side of the ion exchange membrane and/or exposed to the same gaseous environment.

These and other features, advantages, and objects of the present invention will be further understood and appreciated by those skilled in the art by reference to the following specification, claims, and appended drawings.

BRIEF DESCRIPTION OF THE DRAWINGS

Certain embodiments of the present invention are illustrated by the accompanying figures. It will be understood that the figures are not necessarily to scale and that details not necessary for an understanding of the invention or that render other details difficult to perceive may be omitted. It will be further understood that the invention is not necessarily limited to the particular embodiments illustrated herein.

The invention will now be described with reference to the drawings wherein:

FIGS. 2A-2B of the drawings are perspective and exploded perspective representations, respectively, of micro electrode assemblies fabricated in accordance with the present invention;

FIGS. 3A-3D of the drawings are representations of micro electrode assemblies fabricated in accordance with the present invention;

FIGS. 4A-4D of the drawings are representations of micro electrode assemblies associated with reference electrodes fabricated in accordance with the present invention;

DETAILED DESCRIPTION OF THE INVENTION

Figure 1A:
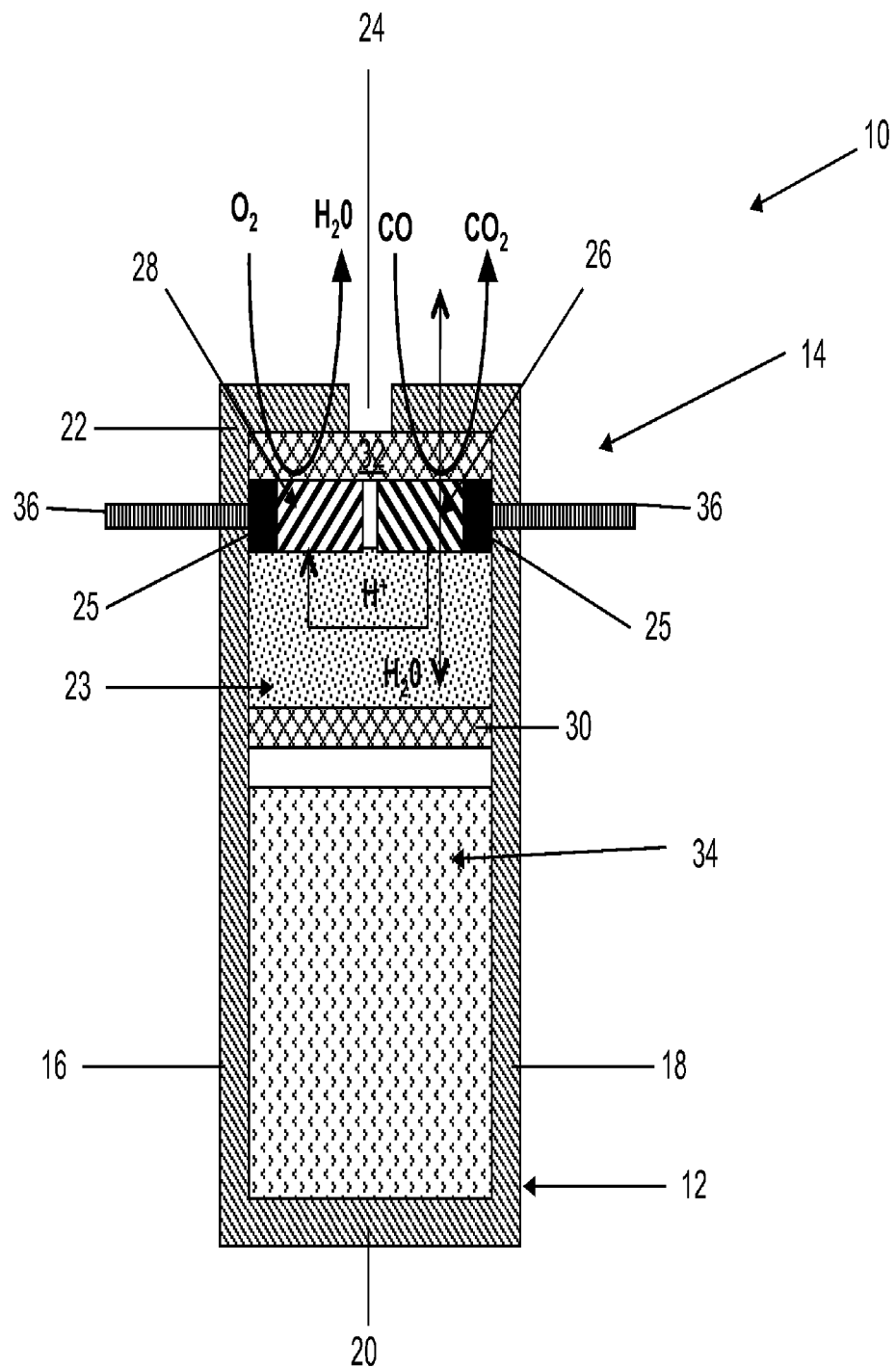
FIG. 1A of the drawings is a cross-sectional schematic representation of an electrochemical sensor fabricated in accordance with the present invention, showing among other things, a solvent reservoir.

Referring now to the drawings and to FIG. 1A in particular, a cross-sectional schematic representation of electrochemical (EC) sensor 10 is shown, which generally comprises housing 12 and micro electrode assembly (MEA) 14.

It will be understood that electrochemical sensor 10 may comprise, for illustrative purposes only, an electrochemical gas sensor for a gas, smoke, and/or fire detector, and the like. It will be further understood that FIG. 1A is merely a schematic representation of electrochemical sensor 10. As such, some of the components may have been distorted from their actual scale for pictorial clarity. Indeed, numerous other electrochemical cell designs and configurations are contemplated for use, including those disclosed in U.S. Pat. No. 4,329,214 entitled "Gas Detection Unit," U.S. Pat. No. 5,302,274 entitled "Electrochemical Gas Sensor Cells Using Three Dimensional Sensing Electrodes," U.S. Pat. No. 5,331,310 entitled "Amperometric Carbon Monoxide Sensor Module for Residential Alarms," U.S. Pat. No. 5,573,648 entitled "Gas Sensor Based on Protonic Conductive Membranes," U.S. Pat. No. 5,618,493 entitled "Photon Absorbing Bio-derived Organometallic Carbon Monoxide Sensors," U.S. Pat. No. 5,650,054 entitled "Low Cost Room Temperature Electrochemical Carbon Monoxide and Toxic Gas Sensor with Humidity Compensation Based on Protonic Conductive Membranes," U.S. Pat. No. 5,944,969 entitled "Electrochemical Sensor With A Non-Aqueous Electrolyte System," U.S. Pat. No. 5,958,200 entitled "Electrochemical Gas Sensor," U.S. Pat. No. 6,172,759 entitled "Target Gas Detection System with Rapidly Regenerating Optically Responding Sensors," U.S. Pat. No. 6,200,443 entitled "Gas Sensor with a Diagnostic Device," U.S. Pat. No. 6,936,147 entitled "Hybrid Film Type Sensor," U.S. Pat. No. 6,948,352 entitled "Self-Calibrating Carbon Monoxide Detector and Method," U.S. Pat. No. 7,077,938 entitled "Electrochemical Gas Sensor," U.S. Pat. No. 7,022,213 entitled "Gas Sensor and Its Method of Manufacture," U.S. Pat. No. 7,236,095 entitled "Solid State Sensor for Carbon Monoxide," U.S. Pat. No. 7,279,081 entitled "Electrochemical Sensor," U.S. Patent Publication No. 2005/0145494 entitled "Liquid Electrochemical Gas Sensor," U.S. Patent Publication No. 2006/0091007 entitled "Gas Detecting Device with Self-Diagnosis for Electrochemical Gas Sensor," U.S. Patent Publication No. 2006/0120924 entitled "Proton Conductor Gas Sensor," and U.S. Patent Publication No. 2006/0196770 entitled "Liquid Electrochemical Gas Sensor," all of which are hereby incorporated herein by reference in their entirety—including all references cited therein.

In accordance with the present invention housing 12 is capable of containing a micro electrode assembly therein, and preferably includes first side wall 16, second side wall 18, and bottom wall 20, which define containment region 23 for containing micro electrode assembly 14 therein, among other sub-components. Housing 12 also preferably includes top wall 22 having gaseous diffusion aperture 24 which allows gasses external to electrochemical sensor 10 to electrochemically interact with micro electrode assembly 14. It will be understood that while housing 12 has been disclosed, for illustrative purposes only, as comprising top wall 22, gaseous diffusion aperture 24 may emanate from first side wall 16 to second sidewall 18, thereby minimizing or eliminating the structural necessity of top wall 22. It will be further understood that top wall 22 may be fabricated from a material different than first side wall 16 and/or second side wall 18, thereby forming a separate and distinct housing cap. As is known in the art, housing 12 may also include filter 32, such as particulate filter and/or activated carbon filter, which enhances the longevity and electrochemical performance of micro electrode assembly 14. In addition housing 12 may optionally include reservoir region 34 which contains/retains solvents/fluids, such as water and/or electrochemical cell redox agents. In a preferred embodiment of the present invention, reservoir region 34 may include a desiccant gel for retaining water or other agents that influence the chemical and/or physical properties of water. Housing 12 also preferably includes electrode leads 36, which enable electrical communication with a sensing circuit.

Figure 1B:
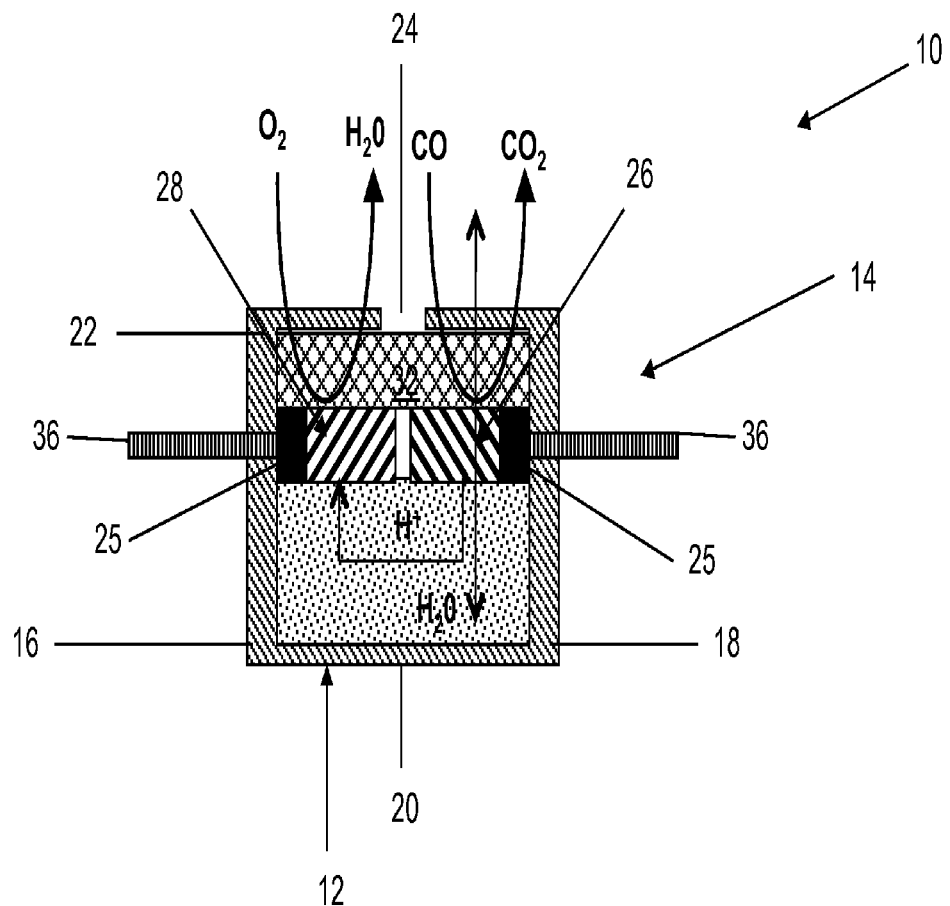
FIG. 1B of the drawings is a cross-sectional schematic representation of a solventless (e.g., waterless) electrochemical sensor fabricated in accordance with the present invention.
Figure 1C:
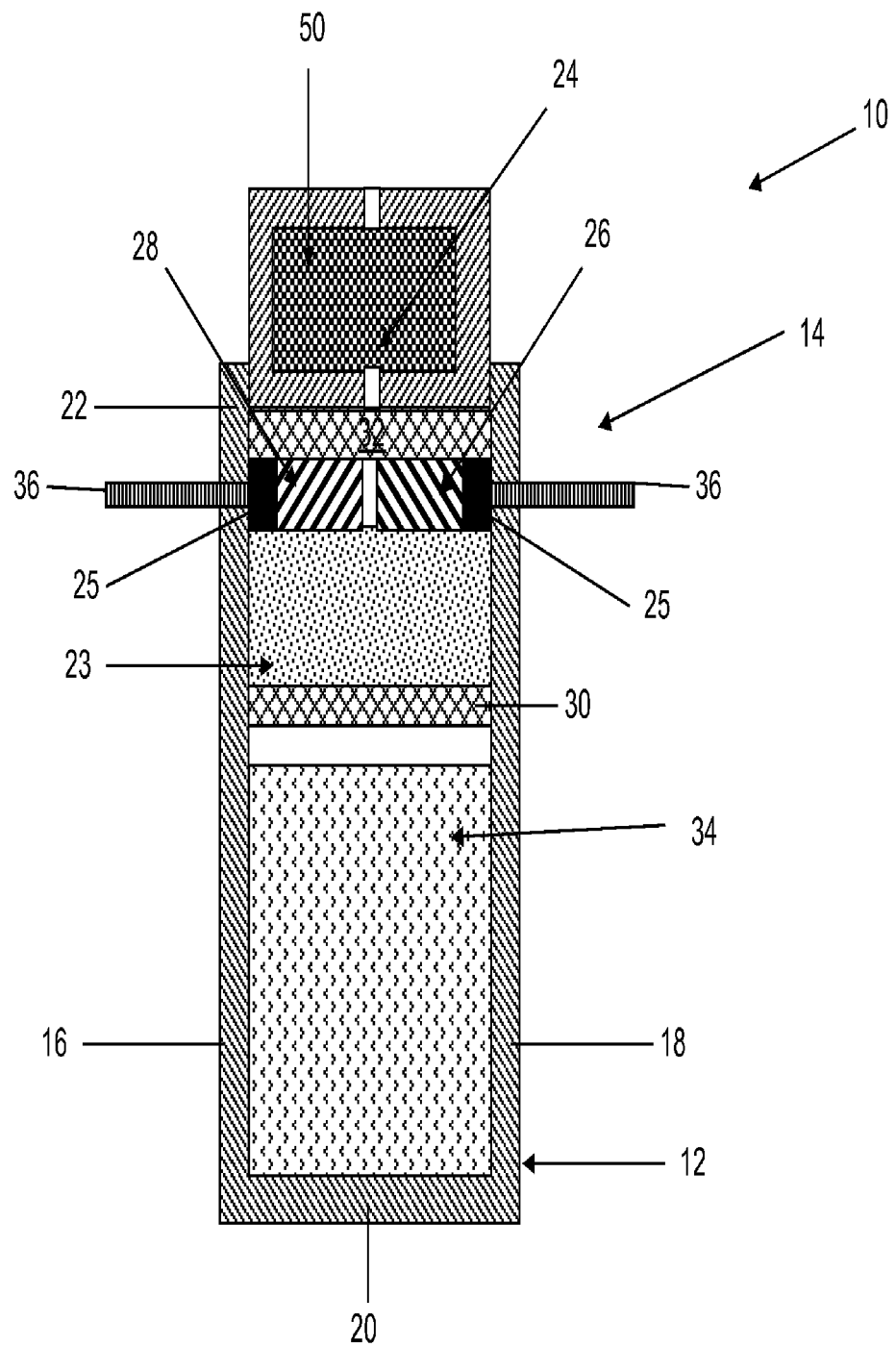
FIG. 1C of the drawings is a cross-sectional schematic representation of an electrochemical sensor fabricated in accordance with the present invention, showing among other things, a top/cover filter.

As is best shown in FIG. 1B, electrochemical sensor 10 may be solventless (e.g., waterless) and void of reservoir region 34. In this embodiment electrochemical sensor 10 may optionally comprise an ion exchange member which preferably comprises $H_3PO_4$ doped polybenzimidazole derivatives, protic ionic liquid doped polybenzimidazole derivatives, and/or protic ionic liquid doped sulfonated polyimide derivatives, which are ionically conductive regardless of the level of ambient humidity/moisture As is best shown in FIG. 1C, electrochemical sensor 10 may further comprise a top or cover filter 50 which covers gaseous diffusion aperture 24 (i.e., the sample gas inlet) and removes unwanted contaminant gases from the sample gas that the sensor may be cross-sensitive to. Additionally cover filter 50 enables the sensor to be washed. Cover filter 50 may comprise an ePTFE (expanded Teflon such as Gore-Tex), a charcoal impregnated felt (Calgon Carbon, Pittsburgh, Pa.), and/or a housing filled with activated charcoal powder or pellets (Calgon Carbon, Pittsburgh, Pa.; Norit Americas Inc., Marshall, Tex.).

For purposes of the present disclosure, housing 12 may be fabricated from one or more of any one of a number of materials including, for example, metals, metallic alloys, pseudo metals, natural and/or synthetic plastics, and composites—just to name a few.

Referring now to FIGS. 1A-1C and 2A-2B, collectively, micro electrode assembly 14 preferably includes anode 26, cathode 28, ion exchange membrane 30, and outer substrate(s) 38 (e.g., a porous Teflon diffusion layer). Individual current collectors 25 are preferably associated with anode 26 and cathode 28, and comprise, for example, carbonaceous conductors such as carbon based conductive paints (XCMC-40, Spraylat Corporation) or conductive carbon loaded silicone rubber (SE65 Conductive Silicone, Stockwell Elastomerics, Inc.) and/or metallic conductors. It will be understood that ion exchange membrane or material 30 generally permits hydrogen or other ion transport between anode 26 and cathode 28, but generally prevents electron conduction between the same. Non-limiting examples of suitable ion exchange membrane materials include, for example, expanded PTFE (Gore, Porex), glass wool, and/or cellulose which may be infused with various ion conducting materials such as mineral acids including $H_2SO_4$, aqueous alkaline salts such as KOH, $H_3PO_4$ doped polybenzimidazole derivatives (L. Xiao, et al., *Fuel Cells* 5 (2005) 287), protic ionic liquid doped polybenzimidazole derivatives, and protic ionic liquid doped sulfonated polyimide derivatives (S.-Y. Lee, et al., *J. Power Sources* (2009))—all of which are hereby incorporated herein by reference in their entirety—including all references cited therein. Other suitable ion exchange membrane materials include solid polymeric electrolytes including, but not limited to, polystyrene sulfonic acid (Sigma-Aldrich) Nafion (Dupont), and/or Flemion (Asahi).

Anode 26 preferably serves as a working or sensing gaseous oxidation electrode, such as a carbon monoxide oxidation electrode which was discussed supra (See for example, ¶0004, and FIG. 1A). Anode 26 may be fabricated from any one of a number of materials including transition metals, alloys, and mixtures of the same. For example, platinum and platinum-ruthenium which can be associated with a carbonaceous species, such as graphene, graphite, amorphous carbon (XC72, BlackPearls), carbon nanotubes (e.g., SWNT, DWNT, MWNT), carbon fibers, and combinations thereof, all of which may be doped with atoms such as, but not limited to, nitrogen, boron, and/or phosphorous—utilizing conventional techniques. Anode 26 may also be associated with an ion conductor, such as Nafion in an analogous manner disclosed infra with regard to the working examples of cathode 28. Additional suitable anodic materials include those disclosed in FUEL CELL FUNDAMENTALS, $2^{nd}$ Ed., O'hayre et al., Wiley (2009), which is hereby incorporated herein by reference in its entirety.

Preferably cathode 28 comprises a cathodic material which includes a carbonaceous material, such as graphene, graphite, amorphous carbon, carbon nanotubes (e.g., SWNT, DWNT, MWNT), carbon fibers, and combinations thereof, all of which may be doped with atoms such as, but not limited to, nitrogen, boron, and/or phosphorous—utilizing conventional techniques, and an oxygen reduction catalyst associated (i.e., chemically and/or physically) with the carbonaceous material. It will be understood that the oxygen reduction catalysts of the present invention are preferably heat treated, pyrolyzed, and/or otherwise activated in a manner which enable the catalysts to remain functionally operable and stable. Notably, the cathodic materials of the present invention preferably do not materially exhibit catalytic activity for the oxidation of carbon monoxide and/or the reduction of carbon dioxide. Cathode 28 may also be associated with an ion conductor, such as Nafion, in an analogous manner disclosed infra with regard to the working examples of the cathode. Such electrochemically selective catalysts enables traditional MEA configurations (e.g., wherein the anode and the cathode of the micro electrode assembly are disposed upon opposite sides of the ion exchange membrane and/or exposed to different gaseous environments (See diagram between ¶¶0005-0006), as well as novel electrode configurations wherein the anode and the cathode of the micro electrode assembly are disposed upon the same side of the ion exchange membrane and/or exposed to the same gaseous environment (See FIGS. 1-5).

In accordance with one embodiment of the present invention, cathode 28 preferably serves as a counter electrode in the MEA and participates in the catalyzed reduction of oxygen to water which was discussed supra (See ¶0004).

Non-limiting examples of suitable oxygen reduction catalysts include a material resulting from pyrolysis of substituted, transition metal (i.e., d-block) porphyrins, unsubstituted transition metal porphyrins, substituted transition metal tetrabenzoporphyrins, unsubstituted transition metal tetrabenzoporphyrins, substituted transition metal tetraphenylporphyrins, unsubstituted transition metal tetraphenylporphyrins, substituted transition metal tetraazaporphyrins, unsubstituted transition metal tetraazaporphyrins, substituted transition metal tetraazamacrocycles, unsubstituted transition metal tetraazamacrocycles, substituted transition metal phthalocyanines, unsubstituted transition metal phthalocyanines, substituted transition metal naphthalocyanines, unsubstituted transition metal naphthalocyanines, substituted transition metal bis(phthalocyanines), unsubstituted transition metal bis(phthalocyanines), substituted transition metal bis(naphthalocyanines), unsubstituted transition metal bis(naphthalocyanines), and/or combinations thereof. Examples of preferred transition metals include, but are not limited to, Co, Cu, Fe, Ir, Ni, Pd, Rh, Ru, or Zn, with Co being the most preferred transition metal.

Suitable oxygen reduction catalysts may also be expressed as comprising a material resulting from pyrolysis of a compound, a structural isomer of a compound, and/or mixtures of isomers of compounds, represented by the following structure:

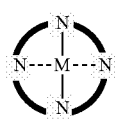

(I)

wherein M comprises a transition metal which is ligated by a tetraazamacrocycle, such as, for example, substituted porphyrins, unsubstituted porphyrins, substituted phthalocyanines, unsubstituted phthalocyanines, substituted naphthalocyanines, unsubstituted naphthalocyanines, and combinations thereof.

By way of non-limiting examples, oxygen reduction catalysts may comprise a material resulting from pyrolysis of a compound, a structural isomer of a compound, and/or mixtures of isomers of compounds, represented by the following structure:

(II)

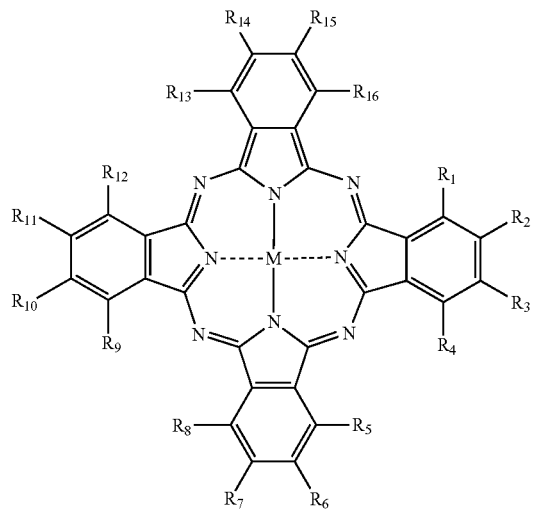

wherein M comprises Co, Cu, Fe, Ir, Ni, Pd, Rh, Ru, or Zn; wherein $R_1$-$R_{16}$ are the same or different and comprise H, $NO_2$, $NH_2$, $NHR_{17}$, $N(R_{18})_2$, $CO_2H$, $CO_2R_{19}$, an alkyl group containing approximately 1 to approximately 10 carbon atom(s), $OR_{20}$, SH, $SR_{21}$, and combinations thereof; and wherein $R_{17-21}$ are the same or different and comprise an alkyl group containing approximately 1 to approximately 10 carbon atom(s).

Three specific phthalocyanines which serve as oxygen reduction catalysts include:

(IIA)

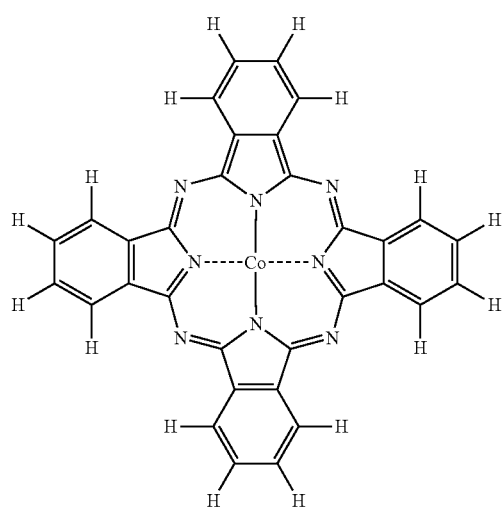

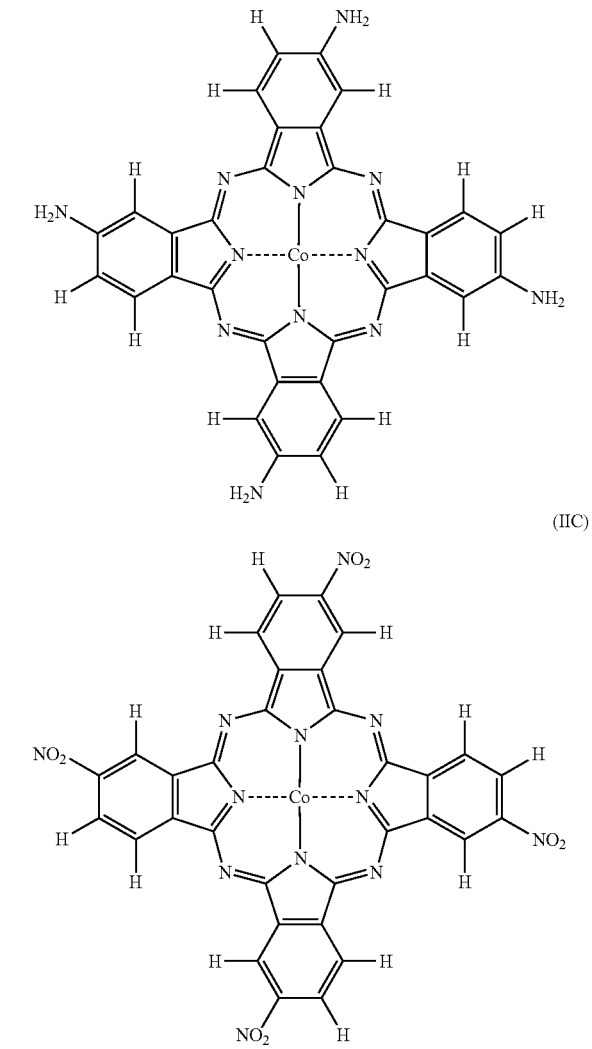

By way of additional non-limiting examples, oxygen reduction catalysts may comprise a material resulting from pyrolysis of a compound, a structural isomer of a compound, and/or mixtures of isomers of compounds, represented by the following formula:

(III)

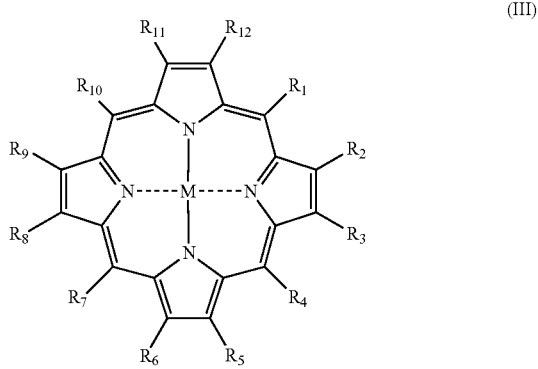

wherein M comprises Co, Cu, Fe, Ir, Ni, Pd, Rh, Ru, or Zn; wherein $R_1$-$R_{12}$ are the same or different and comprise H, $NO_2$, $NH_2$, $NHR_{13}$, $N(R_{14})_2$, $CO_2H$, $CO_2R_{15}$, an alkyl group containing approximately 1 to approximately 10 carbon atom(s), $OR_{16}$, SH, $SR_{17}$, and combinations thereof; and wherein $R_{13-17}$ are the same or different and comprise an alkyl group containing approximately 1 to approximately 10 carbon atom(s).

In one embodiment of the present invention, the oxygen reduction catalyst comprise a material resulting from pyrolysis of a compound, a structural isomer of a compound, and/or mixtures of isomers of compounds, represented by the following formula:

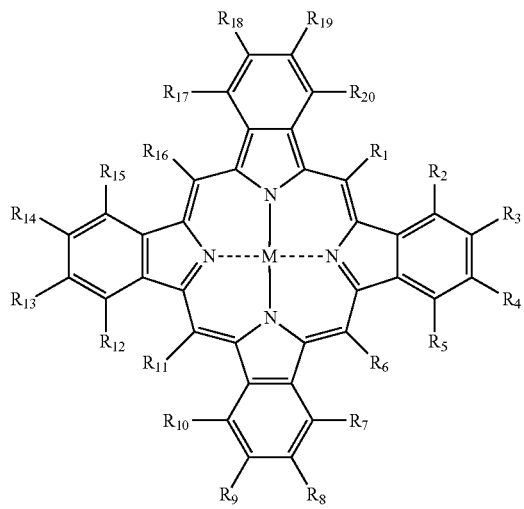

(IV)

wherein M comprises Co, Cu, Fe, Ir, Ni, Pd, Rh, Ru, or Zn; wherein $R_1$-$R_{20}$ are the same or different and comprise H, $NO_2$, $NH_2$, $NHR_{21}$, $N(R_{22})_2$, $CO_2H$, $CO_2R_{23}$, an alkyl group containing approximately 1 to approximately 10 carbon atom(s), $OR_{24}$, SH, $SR_{25}$, and combinations thereof; and wherein $R_{21-25}$ are the same or different and comprise an alkyl group containing approximately 1 to approximately 10 carbon atom(s).

In accordance with another embodiment of the present invention, the oxygen reduction catalysts comprises a material resulting from pyrolysis of a compound, a structural isomer of a compound, and/or mixtures of isomers of compounds, represented by the following formula:

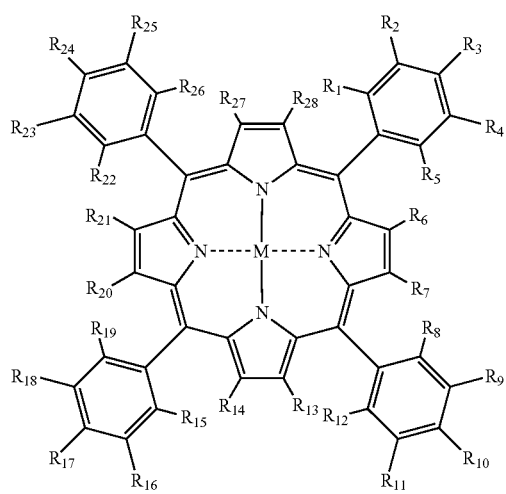

(V)

wherein M comprises Co, Cu, Fe, Ir, Ni, Pd, Rh, Ru, or Zn; wherein $R_1$-$R_{28}$ are the same or different and comprise H, $NO_2$, $NH_2$, $NHR_{29}$, $N(R_{30})_2$, $CO_2H$, $CO_2R_{31}$, an alkyl group containing approximately 1 to approximately 10 carbon atom(s), $OR_{32}$, SH, $SR_{33}$, and combinations thereof; and wherein $R_{29-33}$ are the same or different and comprise an alkyl group containing approximately 1 to approximately 10 carbon atom(s).

In accordance with yet another embodiment of the present invention, the oxygen reduction catalysts comprise a material resulting from pyrolysis of a compound, a structural isomer of a compound, and/or mixtures of isomers of compounds represented by the following formula:

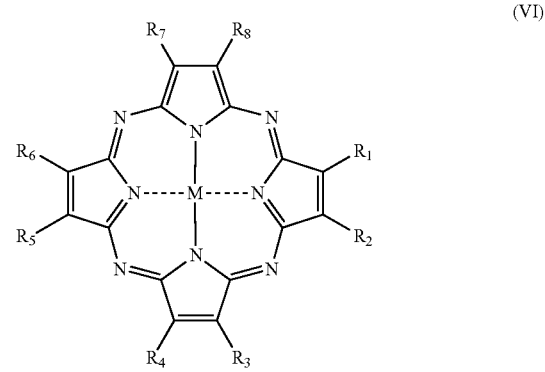

(VI)

wherein M comprises Co, Cu, Fe, Ir, Ni, Pd, Rh, Ru, or Zn; wherein $R_1$-$R_8$ are the same or different and comprise H, $NO_2$, $NH_2$, $NHR_9$, $N(R_{10})_2$, $CO_2H$, $CO_2R_{11}$, an alkyl group containing approximately 1 to approximately 10 carbon atom(s), $OR_{12}$, SH, $SR_{13}$, and combinations thereof; and wherein $R_{9-13}$ are the same or different and comprise an alkyl group containing approximately 1 to approximately 10 carbon atom(s).

It will be understood that several of the above-identified compounds are provided herein as working examples and that additional disclosure for the commercial availability and/or preparation of transition metal porphyrins, tetrabenzoporphyrins, tetraphenylporphyrins, tetraazaporphyrins, tetraazamacrocycles, phthalocyanines, naphthalocyanines, bis (phthalocyanines), and bis(naphthalocyanines), are available from common chemical vendors, such as Sigma-Aldrich Chemical Co., of Milwaukee, Wis. and Strem Chemical of Newburyport, Mass.

Without being bound to any one particular theory, it is believed that the metal atom in M-$N_4$ catalysts disclosed herein contribute to the proper structural formation of the most active carbon-nitrogen catalytic sites during pyrolysis. As such, removal of the metal after pyrolysis using an acid extraction does not appear to adversely affect electrode performance. Suitable acid extraction techniques are provided in, for example, (T. Ikeda, et al., *J. Phys. Chem. C* 112 (2008) 14706, (M. Saito et al., 215*th ECS Meeting*, Abstract #265), and (M. Saito et al., 217*th ECS Meeting*, Abstract #502)—all of which are hereby incorporated herein by reference in their entirety—including all references cited therein. The Examples infra provide further details regarding M-$N_4$ catalysts.

Referring once again to FIGS. 3A-3D, electrochemical sensor 10 preferably includes micro electrode assembly 14, wherein anode 26 and cathode 28 are preferably: (1) disposed upon the same plane, (2) disposed upon the same side of the ion exchange membrane, and/or (3) exposed to a same gaseous environment. It will be understood that, regardless of its ordinary meaning, the term the "same gaseous environment" will be defined herein as the same ambient air, and/or the same air external to the micro electrode assembly. It will be understood that the micro electrode assemblies of the present invention facilitate numerous design configurations not available heretofore. In particular, conventional cathodic materials exhibit catalytic activity for the oxidation of carbon monoxide as well as the reduction of oxygen to water. As such, without restricting the cathode to ambient sample gas, the sensor is susceptible to undesirable failure under a plurality of conditions.

In accordance with the present invention, micro electrode assembly 14 may be fabricated using any one of a number of conventional techniques, including pad or decal printing, as is disclosed in U.S. Pat. No. 5,211,984, which is hereby incorporated herein by reference in its entirety—including all references cited therein, brushing, screen printing, spraying, ink jet printing, and/or dip coating—just to name a few.

It will be understood that a typical fuel cell or electrochemical sensor has an ion exchange or conducting membrane that separates the two electrodes. Typically this membrane is approximately 10-200 µM thick. However, in certain embodiments of the present invention, ions diffuse laterally across the membrane. A long ion diffusion length increases ionic resistance and therefore reduces signal strength. To reduce any undesirable ionic resistance, the ion diffusion length is preferably minimized between the two electrodes, via a narrow gap, and within each electrode, via narrow electrodes. The cross sectional area between the two electrodes is also preferably maximized to enhance current flow and signal strength. Preferentially, the MEA configuration will comprise an interdigitated electrode design similar to that shown in FIGS. 3A and 4A.

It will be further understood that a typical fuel cell or electrochemical sensor has an electron path length that is essentially the thickness of each electrode which is approximately 1-100 µM, before reaching an external current collector. However, in certain embodiments of the present invention, electrons diffuse laterally across the electrodes before reaching the external current collectors. As such, the carbon based materials have a relatively high electron resistance so the path length is preferably minimized to enhance signal strength. Preferentially, the MEA configuration comprises an interdigitated electrode design similar to that shown in FIG. 3A or 4A—wherein electrode finger lengths are optimized to reduce the electron resistance but maintain a high amount of material to maximize the rate of chemical reactions occurring.

In accordance with the present invention, catalysts found in the anode and cathode have different activities and levels of current output towards their respective gases. To reduce wasted material, among other things, the thickness, area, and dimensions of each electrode can be varied. Suitable examples are provided in FIGS. 3A-3D. Preferably the ratio of the two dimensional areas of the cathode to anode is greater than approximately 1:1, and more preferably approximately 2.4:1. In addition, the ratio of the thickness of the cathode to anode preferably greater than approximately 1:1, and more preferably approximately 2:1. It will be understood that during normal operation (carbon monoxide is present and the sensor is sensing), $H_2O$ is generated at the cathode. At high CO concentrations, the produced water can plug the porous network of the carbon electrode thus reducing the activity of the cathode and reducing the signal strength. A cathode of large surface area can be used to wick this water away from the most active regions of the electrode and allow a stable signal to be achieved.

Figure 5:
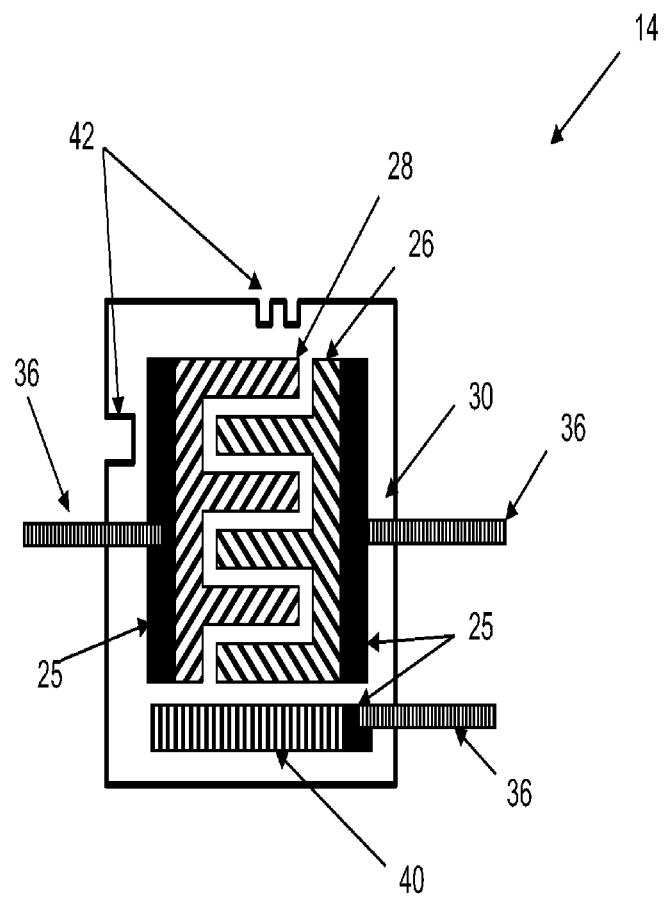
FIG. 5 of the drawings is a representation of a micro electrode assembly having a key member fabricated in accordance with the present invention.

As is best shown collectively in FIGS. 3-5 and Example 15, when a planar design for micro electrode assembly 14 of sensor 10 is utilized, the addition of MWNT to cathodic inks has provided surprisingly beneficial results with respect to enhancing conductivity without adversely affecting catalytic activity.

Referring now to FIGS. 4A-4D, electrochemical sensor 10 may also include one or more reference electrodes 40 associated with micro electrode assembly 14. The reference electrodes facilitate, among other things, long term device performance and sensitivity optimization.

As is best shown in FIG. 5, micro electrode assembly 14 preferably includes key member(s) 42, which regulate orientation and positional engagement relative to housing 12 of electrochemical sensor 10. For example, key member 42 may comprise one or more tabs and/or slots, which matingly correspond to housing 12 for proper positioning during, for example, replacement of micro electrode assembly 14.

In accordance with the present invention sensors preferably comply with alarm specifications set forth in UL 2034.

It will be understood that, unless otherwise specified, the chemical reagents and compounds provided herein below, or their precursors, are available from common commercial chemical vendors, such as Sigma-Aldrich Chemical Co., of Milwaukee, Wis.

The invention is further described by the following examples.

Example 1

Preparation of Tetranitro(Cobalt Phthalocyanine), $CoPc(NO_2)_4$

A 250 mL 3-neck round bottom flask fitted with a thermocouple and reflux condenser was charged with cobalt sulfate heptahydrate (3.4 g, 12.1 mmol), 4-nitrophthalic acid (9.25 g, 43.8 mmol), urea (15 g, 250 mmol), ammonium chloride (1.13 g, 21.1 mmol), and ammonium molybdate tetrahydrate (0.14 g, 0.1 mmol) in 6.5 mL nitrobenzene. The mixture was heated to 185° C. for 5 hours under a blanket of nitrogen. The reddish mixture quickly turned dark blue. The solid was collected on a glass frit filter and washed with 350 mL of warm methanol to remove residual nitrobenzene. The solid was then boiled in 150 mL 1M HCl saturated with NaCl for five minutes. The liquid was removed by filtration then the solid was added to 150 mL 1M NaOH plus 50 g NaCl. The mixture was heated to 90° C. under a light argon flow until ammonia was no longer evolved as checked with damp pH paper. The mixture was cooled and the solid collected by filtration. The solid was alternately washed three times with 1.0M HCl (60 mL) then 1.0M NaOH (60 mL). This was followed by washing with 400 mL water. The solid was dried in a vacuum oven at 70° C. for 24 hours. Yield: 7.86 g=86%

Example 2

Preparation of Tetraamino Cobalt Phthalocyanine, $CoPc(NH_2)_4$

A 50 mL round bottom flask fitted with a condenser was charged with $CoPc(NO_2)_4$ (0.68 g, 0.9 mmol) and sodium sulfide monohydrate (10.4 g, 43.4 mmol) in 15 mL water. The mixture was stirred at room temperature for 72 hours then heated to reflux for 24 hours. After cooling to room temperature, a blue solid was collected by filtration. The solid was washed with 50 mL water then it was dissolved in 100 mL 1M HCl. A small amount of insoluble material was removed by filtration. The filtrate was collected and the pH was raised to >11 by the very careful addition of NaOH pellets. A large amount of greenish-blue precipitate formed which was collected by filtration and washed with copious amounts of water until the filtrate was neutral by pH paper. The solid was dried in a vacuum oven at 70° C. for 24 hours. Yield: 0.28 g=49%

Example 3

Cobalt Phthalocyanine Deposited and Thermally Treated on Multi-walled Carbon Nanotubes, CoPc-MWNT A 50 mL round bottom flask was charged with 100 mg cobalt phthalocyanine (Aldrich), 200 mg MWNT(Cheap Tubes Inc., 10-20 nm diameter, 10-30 μM length, >95% purity), and 25 mL dry DMF. The mixture was sonicated for 40 minutes (750 W, 38% amplitude, 20 seconds on/10 seconds off pulse). The DMF was removed by rotary evaporation. The purple tinted tubes were dried in a vacuum oven at 70° C. for 24 hours. The CoPc deposited tubes (299 mg) were placed in a fused quartz boat and inserted into a tube furnace. The furnace was purged with argon (275 mL/min) for 45 minutes. The argon flow was reduced to 100 mL/min then the furnace was heated to 700° C. That temperature was held for two hours then cooled to room temperature. Final yield: 273 mg. Thermogravimetric analysis, TGA yielded 6.03 wt % residue.

Example 4

Metal-free Phthalocyanine Deposited and Thermally Treated on Multi-wall Carbon Nanotubes, Pc-MWNT A 250 mL conical flask was charged with 222 mg 29H, 31H-phthalocyanine (Aldrich), 667 mg MWNT (Cheap Tubes Inc., 10-20 nm diameter, 10-20 μM length, >95% purity), and 150 mL anhydrous DMF. The mixture was sonicated for 30 minutes (750 W, 50% amplitude, 30 seconds on/10 seconds off pulse) while in an ice bath. The suspension was poured into 800 mL 1:1 hexane/ethyl ether with vigorous stirring. The solid was collected on a 0.45 μM PTFE membrane filter and washed with two portions of 250 mL 1:1 hexane/ethyl ether. The material was transferred to a fused quartz boat and placed in a tube furnace. The solid was dried at 100° C. under a flow of anhydrous argon at 235 mL/min for 90 minutes. The argon flow was reduced to 65 mL/min then the temperature ramped to 700° C. and held there for 120 minutes. After cooling to room temperature, 730 mg of catalyst was yielded.

Example 5

Sample Preparation, $CoPc(NH_2)_4$-MWNT/Nafion 5.0 mg $CoPc(NH_2)_4$-MWNT was suspended in 10.0 mL 1:1 ethanol/water. The mixture was sonicated for 10 minutes (750 W, 30% amplitude, 20 sec on/10 sec off pulse). 40.0 μL 5% Nafion solution was added. The suspension was sonicated for an additional 2 minutes under the above conditions. 20.0 μL of the black suspension was carefully deposited onto only the glassy carbon of a RDE electrode (Pine Instruments, 5.0 mm diameter) and allowed to dry. All samples were prepared in a similar manner.

Experimental Parameters 0.5M $H_2SO_4$ was used as an electrolyte. The counter electrode was platinum mesh and the reference electrode was a double junction Ag/AgCl electrode.

Initial Activities for Oxygen Reduction by Cyclic Voltammetry

Figure 6:
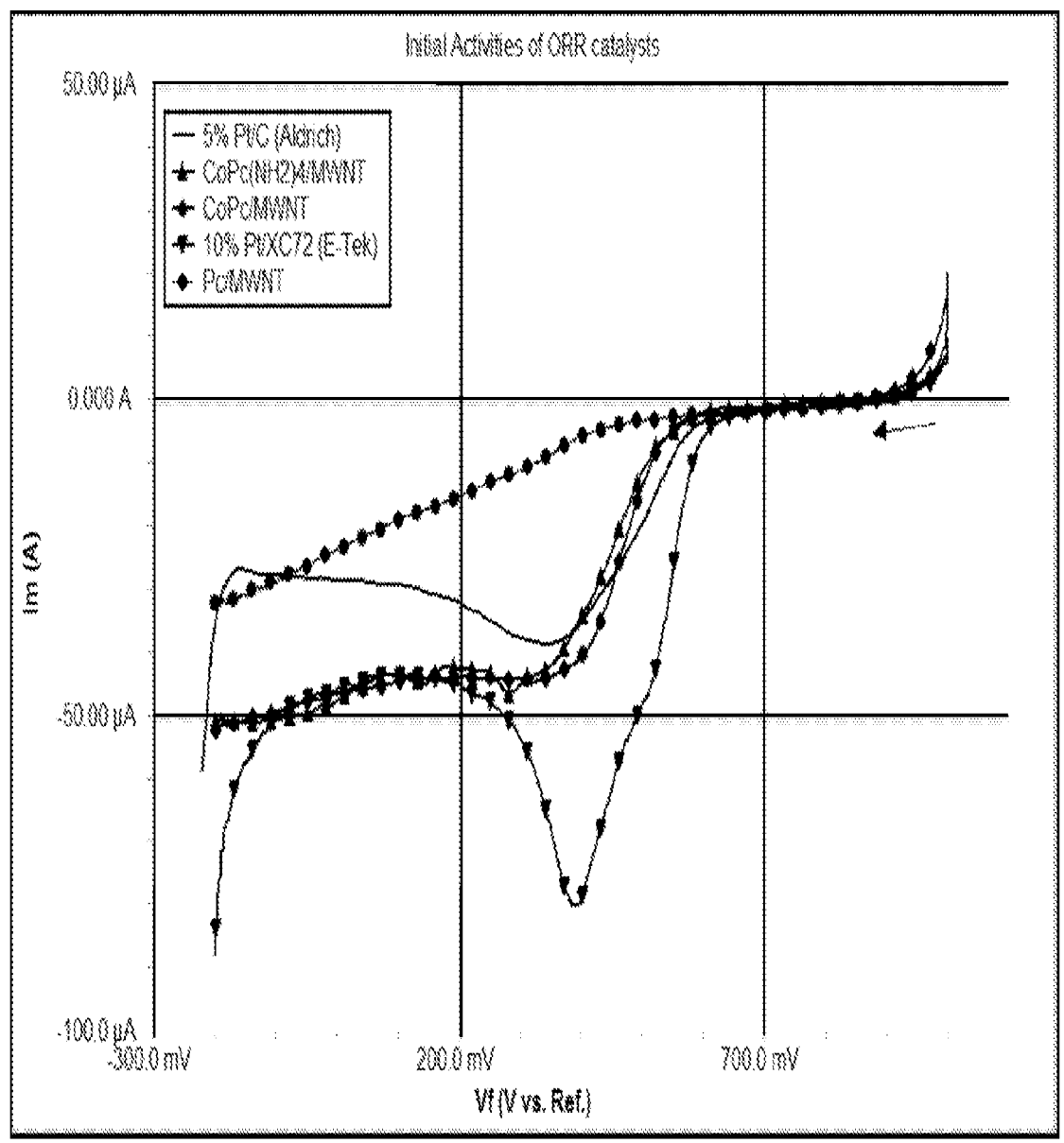
FIG. 6 of the drawings is a cyclic voltammagram verifying that embodiments of the present invention are electrochemically active towards the reduction of oxygen.

The electrolyte was purged with oxygen then the sample was scanned from 1.0 to −0.2V at 10 mV/s to determine the initial activity of the sample. This was repeated for several cobalt phthalocyanines on both MWNT and commercially available XC72 carbon. A state of the art fuel cell catalyst, 10 wt % Pt/XC72 (E Tek) was also included as was 5 wt % Pt/carbon (Aldrich). See FIG. 6 for results. Activity is determined by the onset of current. As shown in FIG. 6, the 10 wt % Pt/XC72 was the most active though all the cobalt based catalysts were nearly as active, which verifies that a broad spectrum of novel cobalt based catalysts exhibit sufficient electrochemical activity. The nitrogen doped nanotubes, N-MWNT, showed very little activity.

Carbon Monoxide Activity

Figure 7:
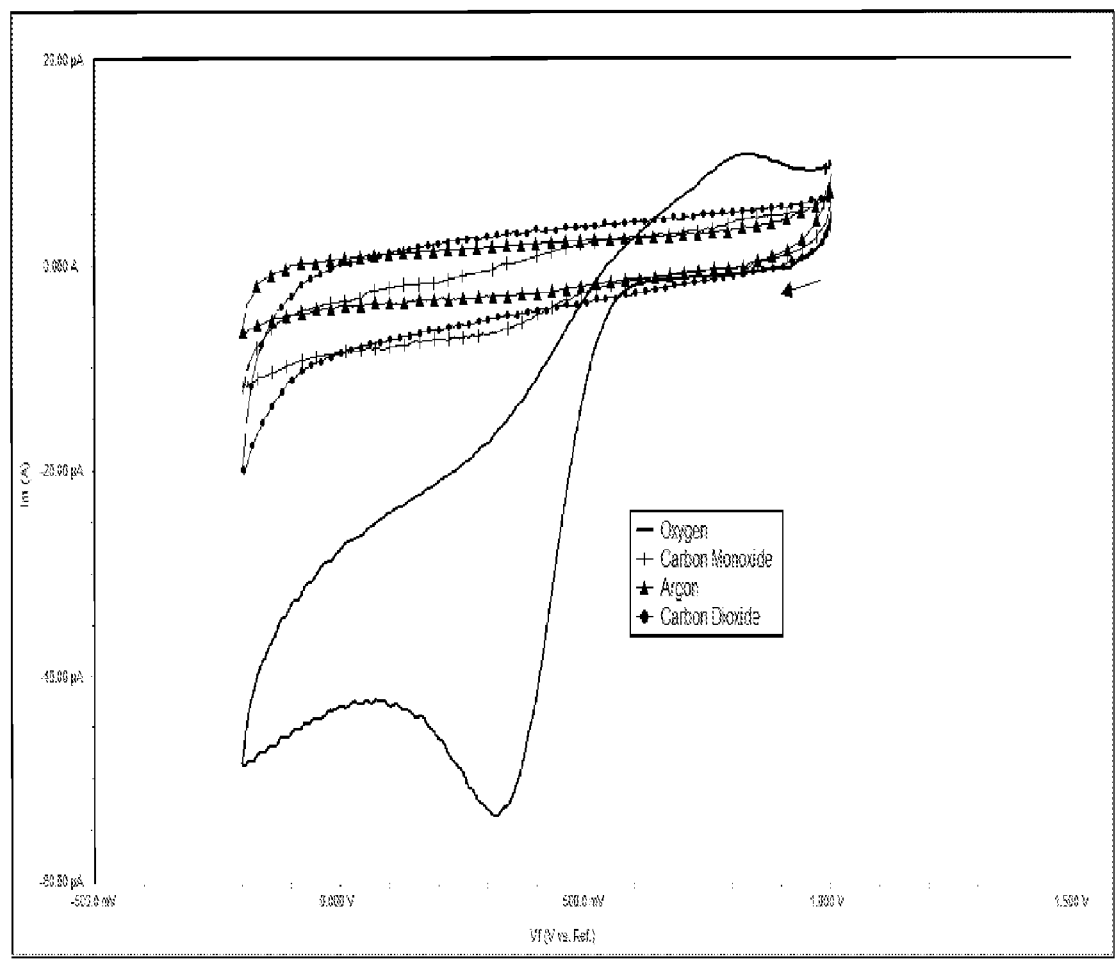
FIG. 7 of the drawings is a cyclic voltammagram verifying that oxygen reduction catalysts of the present invention are materially electrochemically inactive with regard to the oxidation of carbon monoxide and the reduction of carbon dioxide.

Unlike platinum based catalysts which are active in both the reduction of oxygen and the oxidation of various fuels, such as hydrogen, methanol, or carbon monoxide, the cobalt-nitrogen based catalysts disclosed herein have been developed to operate only as ORR catalysts. To check for activity for the catalytic oxidation of carbon monoxide, a sample of $CoPc(NO_2)_4$—XC72/Nafion was studied. Identical conditions to study the ORR activity were used with the exception that the electrolyte was purged with carbon monoxide for 30 minutes. The sample was scanned from −0.2 to 1.0 to −0.2V at 10 mV/s. See FIG. 7 for results. The scan under carbon monoxide was almost identical to that under argon, an inert gas. There was essentially no activity. Subsequent scanning under carbon dioxide also revealed inactivity for the reduction of carbon dioxide.

Example 6

Molecular Activation of MWNT 10 wt % PCA-MWNT: A 500 mL round bottom flask was charged with 130 mg 1-pyrenecarboxylic acid (PCA) (Sigma-Aldrich), 1.18 g MWNT (Cheap Tubes Inc, 10-20 nm diameter, 10-30 μM length, >95% purity), and 180 mL ethanol. The mixture was sonicated for one hour (750 W, 50% amplitude, 20 s on/10 s off pulse). The suspension was allowed to sit for 48 hours then the solid was collected by filtration on a 0.2 μM PTFE membrane filter. The solid was washed with 120 mL ethanol then dried under vacuum at 70° C. for 24 hours. TGA yielded 0.7% ash, a typical value for this batch of MWNT.

Example 7

Preparation of Anodic Catalyst I 10.5 wt % Pt/PCA-MWNT: A 50 mL Erlenmeyer flask was charged with 50 mg 10 wt % PCA-MWNT in 25 mL 5% $H_2O$ in ethylene glycol. The suspension was sonicated for 10 minutes (750 W, 30% amplitude, 20 s on/10 s off pulse). To this suspension was added 14 mg $H_2PtCl_6$ (Sigma-Aldrich) in 5 mL 5% $H_2O$ in ethylene glycol over 3 minutes with vigorous stirring. After 10 minutes of stirring, the suspension was sonicated under the above conditions for 3 minutes. A few Teflon chips were added to the suspension which was then heated in a microwave for two minutes (2450 MHz, 1000 W, 50% power) under nitrogen. After cooling to room temperature, the suspension was diluted with 30 mL ethanol and the solid was collected by filtration on a 0.2 μM PTFE membrane filter. The product was washed with 100 mL ethanol then dried in a vacuum oven at 70° C. for 16 hours. TGA yielded 10.5 wt % Pt.

Example 8

Preparation of Anodic Catalyst II 9.6 wt % Pt/PCA-MWNT: A 1-L Erlenmeyer flask was charged with 1.25 g PCA-MWNT in 540 mL 5% $H_2O$ in ethylene glycol. The modified nanotubes were suspended in the solvent by sonication for 120 minutes (750 W, 50% amplitude, 30 s on/10 s off pulse). The suspension was transferred to a 1-L round bottom flask. A magnetic stir bar was added to the flask. Under vigorous stirring, 347 mg $H_2PtCl_6$ (Sigma-Aldrich, 40 wt % Pt) in 10 mL 5% $H_2O$ in ethylene glycol was added over one minute. Stirring was continued for 2 hours. The flask was then fitted with a reflux condenser under a blanket of nitrogen and placed in microwave (Milestone Ethos, 1200 W). Under full power and magnetic stirring, the suspension temperature was ramped to reflux at 165° C. in 4 minutes and was held there for an additional 8 minutes. After cooling to room temperature, the suspension was diluted with 500 mL ethanol then collected by filtration on a 0.45 μM PTFE membrane filter. The filtrate was washed with two portions of 200 mL ethanol each followed by drying under vacuum at 70° C. for 16 hours. TGA yielded 9.6 wt % Pt. Powder XRD on a similarly prepared sample yielded an average Pt nanoparticle size of 3.3 nm by examination of the Pt[200] peak.

Example 9

Preparation of Anode Ink 10.2 wt % Pt/PCA-MWNT was finely ground using an agate mortar and pestle. A 125 mL Erlenmeyer flask was charged with 254 mg 10.2 wt % Pt/PCA-MWNT, 6.5 g glycerol (Sigma-Aldrich), 865 mg water (18.2 MΩ-cm, Millipore), and 8.5 g 1-propanol (Sigma-Aldrich). Approximately 60 g of excess 1-propanol was then added. The catalyst was suspended by sonication for 60 minutes (750 W, 50% amplitude, 30 s on/10 s off pulse). 850 mg Nafion solution (10 wt % in $H_2O$, Fuel Cell Store) diluted in 11 g 1-propanol was added to the suspension. The suspension was sonicated for an additional five minutes under the conditions listed previously. A magnetic stir bar was placed in the flask and the suspension was vigorously stirred for 16 hours. The suspension was transferred to a tared bottle and concentrated using heat and a flow of dry argon, until 2 wt % solids was reached. 80 μL tetrabutylammonium hydroxide (TBA-OH) (1.0M in methanol, Sigma-Aldrich) was added to covert the acidic Nafion to the heat stable $TBA^+$ form. After removal of volatiles, an electrode consisting of 67 wt % (Pt/PCA-MWNT) and 33 wt % Nafion results.

Example 10

Preparation of Cathode Ink

A 250 mL pear shaped flask was charged with 150 mg $CoPc(NO_2)_4$-MWNT, 150 mg MWNT (Cheap Tubes Inc., Brattleboro, Vt.), 83 mg PTFE dispersion (0.1-1.0 μM, 60 wt % in $H_2O$, Ion-Power Inc.), 9.60 g glycerol, 2.09 g $H_2O$, and 12.18 g 1-propanol. Approximately 125 g of excess 1-propanol was added. The mixture was sonicated for 120 minutes (750 W, 50% amplitude, 30 s on/10 s off pulse) while cooled in an ice bath. A magnetic stirbar was added to the suspension and under vigorous stirring, 668 mg Nafion solution (15 wt % in aqueous alcohols, Liquion LQ-1115, Ion-power Inc., New Castle, Del.) was added. The suspension was mixed for two hours then sonicated for five minutes under the above conditions. 141 μL tetrabutylammonium hydroxide solution (1.0M in methanol, Sigma-Aldrich) was added then the suspension was sonicated for five minutes under the above conditions. The suspension was concentrated by rotary evaporation then transferred to a tared bottle and concentrated further with heat until a 2 wt. % solids suspension was achieved. After removal of volatiles, an electrode consisting of 30.0 wt % (33% $Co(Pc(NO_2)_4$/MWNT), 30.0 wt % MWNT, 20 wt % Nafion, and 20 wt % PTFE results.

Example 11

Preparation of $Na^+$-Nafion 117

A 8 cm×11 cm piece of Nafion 117 membrane (Dupont) was placed in 275 mL water purified by reverse osmosis at 90° C. for 120 minutes. The membrane was quickly rinsed with water then placed in 275 mL 3% $H_2O_2$ at 90° C. for 60 minutes. The membrane was rinsed with water for 10 minutes then converted to the Na+ form by placing it into 275 mL 1M NaOH for 120 minutes. The membrane was rinsed with water for 15 minutes and allowed to air dry. After cutting into pieces of the desired size, it was stored at room temperature in water (18.2 MΩ-cm, Millipore).

Example 12

Decal Preparation

A stamp of pattern similar to FIG. 3C is machined from a 1 cm thick block of Teflon. The stamp dimensions are approximately 1 cm×0.7 cm with a 0.1 cm gap between the two electrodes. A light coating of PTFE mold release is applied to the stamp. Using a micropipette, anodic ink (10% Pt/PCA-MWNT/Nafion, 2 wt % solids) is applied to the anode in a volume of 100-1000 μL/cm², preferably 150-300 μL/cm². Using a micropipette, cathodic ink (1:1(33% $Co(Pc(NO_2)_4$/MWNT)/MWNT/Nafion, 2 wt % solids) is applied to the cathode in a volume of 100-1000 μL/cm², preferably 150-300 μL/cm². The stamp is dried at 50-250° C., preferably 180° C. A flow of dry nitrogen across the part or application of vacuum may be used in addition to heat to speed drying of the ink. A second layer of anodic ink is applied to the anode for a total of two. Three additional layers of cathodic ink is applied to the cathode for a total of four. Identical drying procedures as listed previously are used to dry each individual layer of ink.

Example 13

Heat Pressing Decal onto Ion-Exchange Membrane

A 1.5 cm×1.5 cm piece of Nafion 117 membrane (Dupont) in the $Na^+$ form is placed on top of the decal coated Teflon stamp. A piece of PTFE coated stainless steel sheet is placed on top the ion-exchange membrane. The assembly is then placed in a heat press set to 195° C. Pressure (47 atm) is applied to the assembly for 120 seconds. The assembly is removed from the press and allowed to cool. The ion-exchange membrane is slowly peeled away from the Teflon stamp. Ideally all of the ink will have transferred from the stamp to the membrane.

Example 14

MEA Acidification and Rehydration

The prepared MEA is placed into a volume of 20-100 mL of 0.1M $H_2SO_4$. It is heated to 60-100° C., preferably 80-90° C. for 1-16 hours. The 0.1M $H_2SO_4$ is decanted and this step may optionally be repeated. The MEA is then rinsed with $H_2O$ purified by reverse osmosis and placed into a volume of 20-100 mL of $H_2O$. It is heated to 60-100° C., preferably 80-90° C. for 1-16 hours. The MEA is rinsed a final time with $H_2O$ purified by reverse osmosis then stored flat between two absorbent sheets until use.

Example 15

Addition of MWNT to Cathodic Inks

A stamped electrode on a Nafion membrane prepared from a 2 wt % solids ink containing 1.5 wt % (20% $Co(Pc(NO_2)_4$/MWNT) and 0.5 wt % Nafion resulted in an average resistance of 35-70 kΩ/cm. To reduce the resistance of the electrodes, some of the catalytic carbon material was replaced with pure MWNT. A stamped electrode of similar cross-sectional area on a Nafion membrane was prepared from a 2 wt % solids ink containing 0.75 wt % (33% $Co(Pc(NO_2)_4$/MWNT), 0.75 wt % MWNT (Cheap Tubes Inc., 10-20 nm diameter, 10-30 μM length, >95% purity) and 0.5 wt % Nafion. The average resistance was 2 kΩ/cm. Both electrodes contained approximately the same amount of cobalt-$N_4$ catalyst. It was discovered that that the pyrolysis step dramatically decreased the conductivity of the MWNT carbon support—possibly due to coating the tubes with $CoPc(NO_2)_4$ which is then pyrolyzed to form a catalytically active but electrically insulating layer of partially-graphitized carbon and nitrogen along with a small amount of cobalt. This coating which has a lower electronic conductivity than the original, highly graphitic MWNT. By blending the pyrolyzed catalyst with pure MWNT, the electronic conductivity can be enhanced without affecting the catalytic activity.

Example 16

Addition of PTFE to Cathodic Inks

In the cathode of a fuel cell or sensor, $H_2O$ is typically generated. At high currents normally found in fuel cells, this $H_2O$ can cause flooding of the pores within the electrode and effectively reduce the amount of oxygen that can reach the catalyst active sites. Known solutions include careful regulation of the flow rate and/or humidity in the oxygen or air feed which requires a sophisticated level of control and supplementary equipment. Though sensors never operate under high current conditions like fuel cells, they have near zero rates of airflow which limits the removal of excess water by evaporation. Sensors are also open systems, exposed to the environment, and must deal with variations in ambient humidity. As such, a sophisticated level of control and supplementary equipment is not an option in a typical sensor application. A simplified method of addressing the removal of excess $H_2O$ in gas sensors is to make the electrode more hydrophobic by the addition of PTFE. Suitable PTFE addition techniques are provided in, for example, U.S. Pat. No. 6,800,391—which is hereby incorporated herein by reference in its entirety—including all references cited therein. Moreover, with the addition of PTFE, pore sizes within the electrode and the availability of the gas to the active site can be controllably modified.

Example 17

Performance of Sensors I and II

Figure 8A:
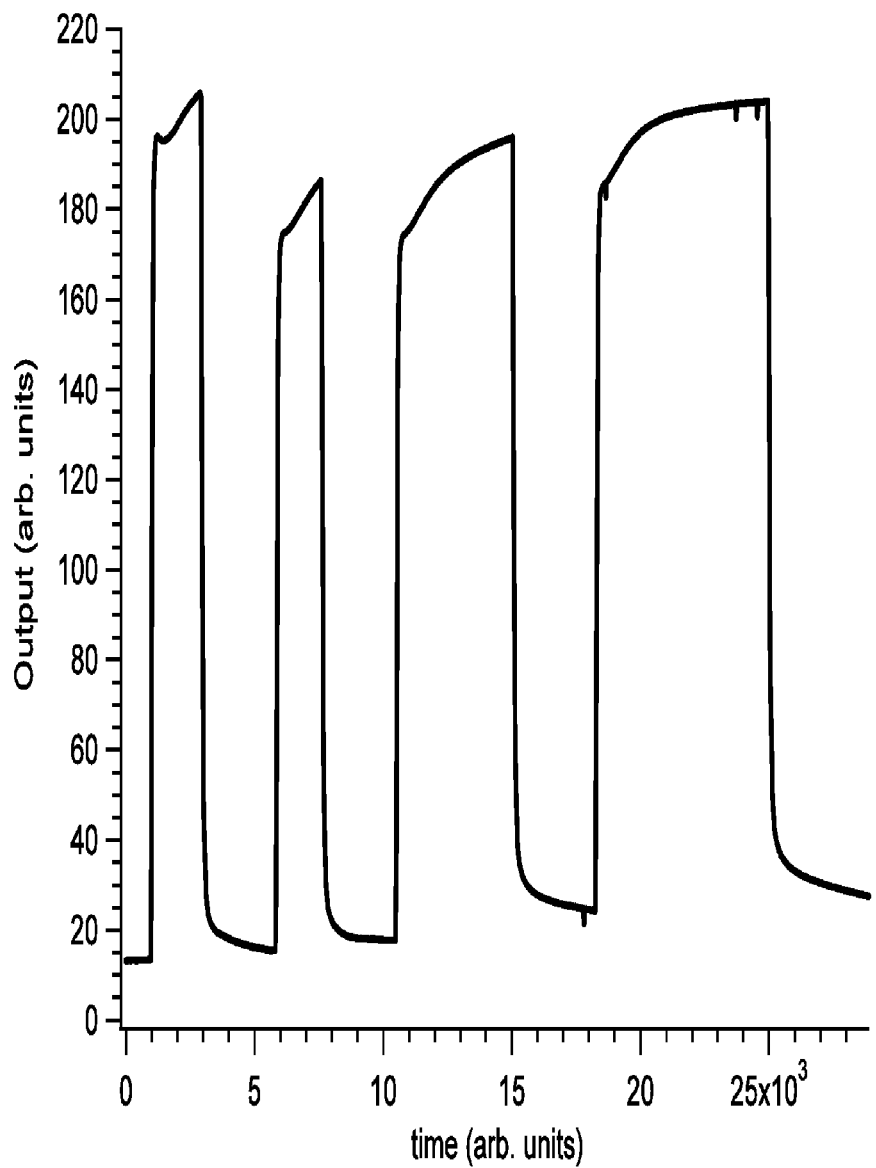
FIG. 8A-8B of the drawings are two-dimensional plots showing sensor performance output as a function of exposure time to pulsed CO.
Figure 8B:
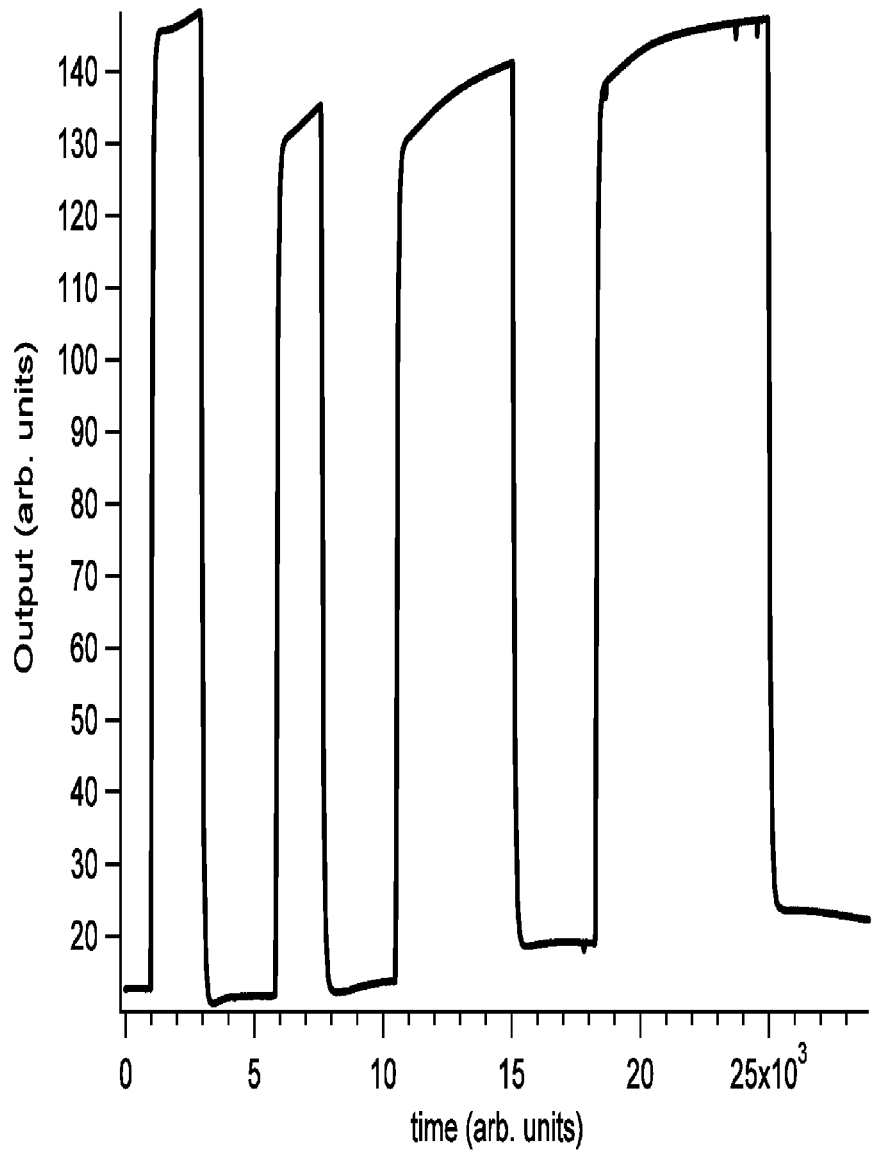

As is shown in FIGS. 8A and 8B, both Sensors I and II, which were fabricated in accordance with the present invention, exhibited well defined performance characteristics toward compliance with alarm specifications set forth in UL 2034.

Example 18

Sensor Calibration

Figure 9:
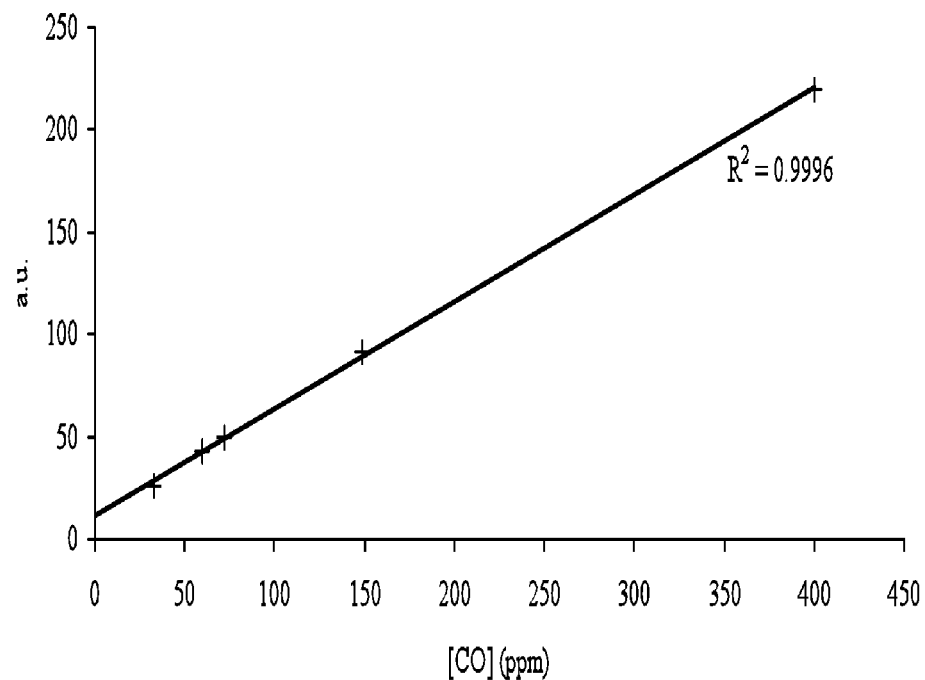
FIG. 9 of the drawings is a two-dimensional plot showing a linear response of a sensor fabricated in accordance with the present invention.
Figure 10:
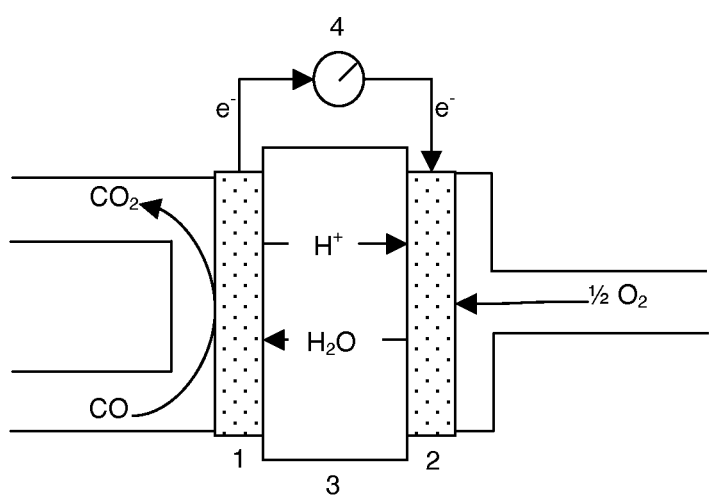
FIG. 10 of the drawings is a representation of a prior art micro electrode assembly.

As is shown in FIG. 9, sensors prepared in accordance with the present invention can surprisingly be calibrated with an ideal two-point calibration. It will be understood that normal sensor calibrations require mathematical fits having computations substantially more complex than the displayed linear calibration.

While the invention has been described in detail herein in accordance with certain preferred embodiments thereof, many modifications and changes therein may be effected by those skilled in the art. Accordingly, it is our intent to be limited only by the scope of the appending claims and not by way of details and instrumentalities describing the embodiments shown herein.

What is claimed and desired to be secured by Letters Patent of the United States is:

1. An electrochemical carbon monoxide sensor for use in a gas or fire detector, the sensor comprising a first sidewall; a second sidewall; a top wall; and a bottom wall; the first sidewall, the second sidewall, the top wall and the bottom wall defining a containment region and containing therein a micro electrode assembly;
wherein:
    the top wall comprises a gaseous diffusion aperture;
    the containment region is void of a solvent reservoir;
    the micro electrode assembly comprises an anode, a cathode, and an ion exchange membrane;
    the electrochemical carbon monoxide sensor is configured to be exposed to a sample gas during a normal sensing operation; and
    the anode and cathode are configured to be exposed to the same sample gas at the same time during the normal sensing operation;
wherein:
    the ion exchange membrane comprises an acid doped polybenzimidazole, an acid doped polypyridylbenzimidazole, a protic ionic liquid doped polybenzimidazole, a protic ionic liquid doped sulfonated polyimide, a polyfluorinated sulfonic acid, or a combination of any two or more thereof;
    the ion exchange membrane permits ion transport between the anode and the cathode, the ion exchange membrane prevents electron conduction between the anode and the cathode;

the cathode comprises an oxygen reduction catalyst, the oxygen reduction catalyst comprising a pyrolysis product of a carbonaceous material and a coordination complex, the coordination complex comprising a transition metal and a nitrogen-containing macrocycle;

the oxygen reduction catalyst does not materially exhibit catalytic activity for the oxidation of carbon monoxide.

2. The electrochemical carbon monoxide sensor of claim 1, wherein the coordination complex is a transition metal porphyrin, a transition metal tetrabenzoporphyrin, a transition metal tetraphenylporphyrin, a transition metal tetraazaporphyrin, a transition metal tetraazamacrocycle, a transition metal phthalocyanine, a transition metal naphthalocyanine, a transition metal bis(phthalocyanine), a transition metal bis(naphthalocyanine), a ion metal bis(naphthalocyanines), or a combination of any two or more thereof.

3. The electrochemical carbon monoxide sensor of claim 1, wherein the coordination complex is a cobalt porphyrin, a cobalt tetrabenzoporphyrin, a cobalt tetraphenylporphyrin, a cobalt tetraazaporphyrin, a cobalt tetraazamacrocycle, a cobalt metal phthalocyanine, a cobalt naphthalocyanine, a cobalt bis(phthalocyanine), a cobalt bis(naphthalocyanine), or a combination of any two or more thereof.

4. The electrochemical carbon monoxide sensor of claim 1, wherein the coordination complex comprises a compound of a transition metal ligated by a tetraazamacrocycle.

5. The electrochemical carbon monoxide sensor according to claim 1, wherein the coordination complex comprises a compound represented by Formula II:

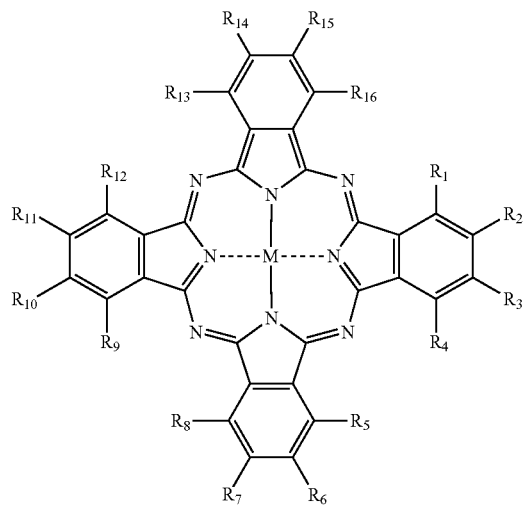

(II)

wherein:
M is Co, Cu, Fe, Ir, Ni, Pd, Rh, Ru, or Zn;
$R_1$-$R_{16}$ are individually H, $NO_2$, $NH_2$, an amine, $CO_2H$, an ester, a $C_1$-$C_{10}$ alkyl, an ether, SH, or a thioether.

6. The electrochemical carbon monoxide sensor of claim 5, wherein M is Co and $R_1$-$R_{16}$ are H.

7. The electrochemical carbon monoxide sensor of claim 5, wherein M is Co; and
$R_1$-$R_{16}$ individually H, $NO_2$, or $NH_2$.

8. The electrochemical carbon monoxide sensor of claim 5, wherein M is Co; and
$R_1$-$R_{16}$ individually H or $NH_2$.

9. The electrochemical carbon monoxide sensor of claim 5, wherein M is Co; and
$R_1$-$R_{16}$ individually H or $NO_2$.

10. The electrochemical carbon monoxide sensor of claim 5, wherein M is Co; $R_3$, $R_7$, $R_{11}$, and $R_{15}$ are $NH_2$; and $R_1$, $R_2$, $R_4$, $R_5$, $R_6$, $R_8$, $R_9$, $R_{10}$, $R_{12}$, $R_{13}$, $R_{14}$, and $R_{16}$ are H.

11. The electrochemical carbon monoxide sensor of claim 5, wherein M is Co; $R_3$, $R_7$, $R_{11}$, and $R_{15}$ are $NO_2$; and $R_1$, $R_2$, $R_4$, $R_5$, $R_6$, $R_8$, $R_9$, $R_{10}$, $R_{12}$, $R_{13}$, $R_{14}$, and $R_{16}$ are H.

12. The electrochemical carbon monoxide sensor of claim 1, wherein the coordination complex is a compound represented by Formula III:

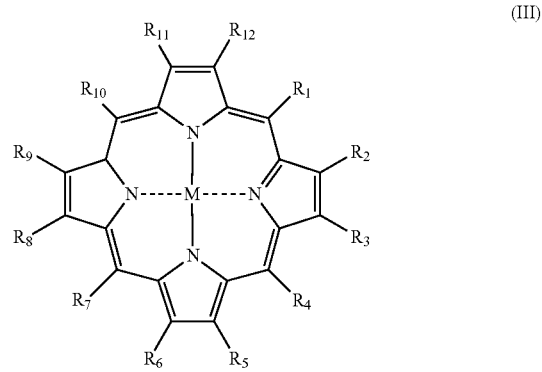

(III)

wherein:
M is Co, Cu, Fe, Ir, Ni, Pd, Rh, Ru, or Zn;
$R_1$-$R_{12}$ are individually H, $NO_2$, $NH_2$, an amine, $CO_2H$, an ester, a $C_1$-$C_{10}$ alkyl, an ether, SH, or a thioether.

13. The electrochemical carbon monoxide sensor of claim 1, wherein the coordination complex is a compound represented by Formula IV:

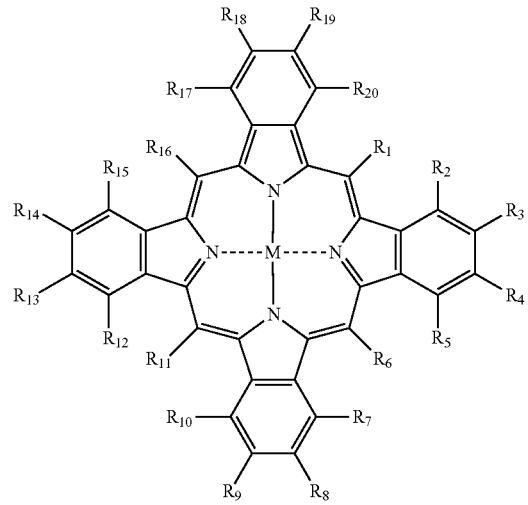

(IV)

wherein:
M is Co, Cu, Fe, Ir, Ni, Pd, Rh, Ru, or Zn;
$R_1$-$R_{20}$ are individually H, $NO_2$, $NH_2$, an amine, $CO_2H$, an ester, a $C_1$-$C_{10}$ alkyl, an ether, SH, or a thioether.

14. The electrochemical carbon monoxide sensor of claim 1, wherein the coordination complex is a compound represented by Formula V:

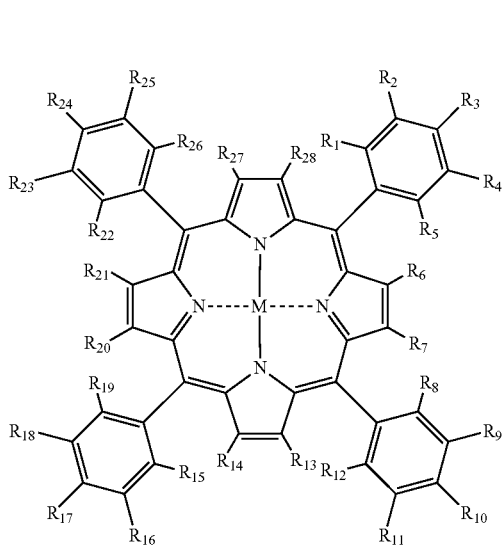

(V)

wherein:
  M is Co, Cu, Fe, Ir, Ni, Pd, Rh, Ru, or Zn;
  $R_1$-$R_{28}$ are individually H, $NO_2$, $NH_2$, an amine, $CO_2H$, an ester, a $C_1$-$C_{10}$ alkyl, an ether, SH, or a thioether.

15. The electrochemical carbon monoxide sensor of claim 1, wherein the coordination complex is a compound represented by Formula VI:

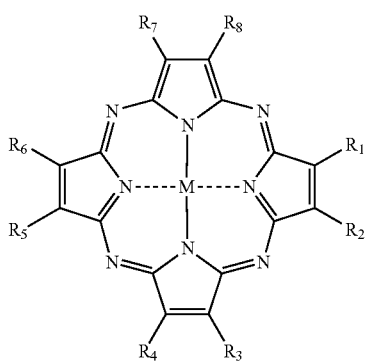

(VI)

wherein:
  M is Co, Cu, Fe, Ir, Ni, Pd, Rh, Ru, or Zn;
  $R_1$-$R_8$ are individually H, $NO_2$, $NH_2$, an amine, $CO_2H$, an ester, a $C_1$-$C_{10}$ alkyl, an ether, SH, or a thioether.

16. The electrochemical carbon monoxide sensor of claim 1, wherein the coordination complex is a compound represented by Formula II-VI, or a combination of any two or more thereof:

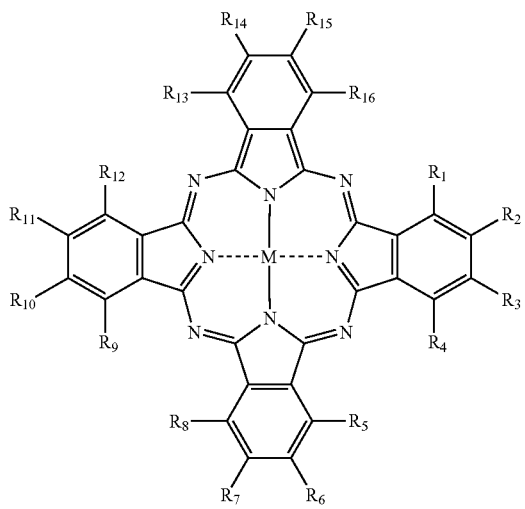

(II)

wherein:
  M is Co, Cu, Fe, Ir, Ni, Pd, Rh, Ru, or Zn;
  $R_1$-$R_{16}$ are individually H, $NO_2$, $NH_2$, an amine, $CO_2H$, an ester, a $C_1$-$C_{10}$ alkyl, an ether, SH, or a thioether;

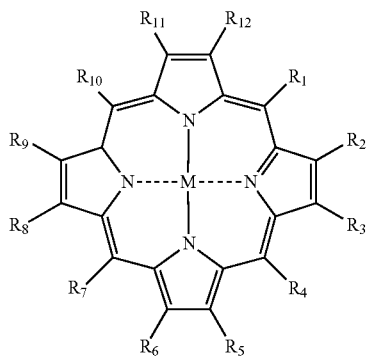

(III)

wherein:
  M is Co, Cu, Fe, Ir, Ni, Pd, Rh, Ru, or Zn;
  $R_1$-$R_{12}$ are individually H, $NO_2$, $NH_2$, an amine, $CO_2H$, an ester, a $C_1$-$C_{10}$ alkyl, an ether, SH, or a thioether;

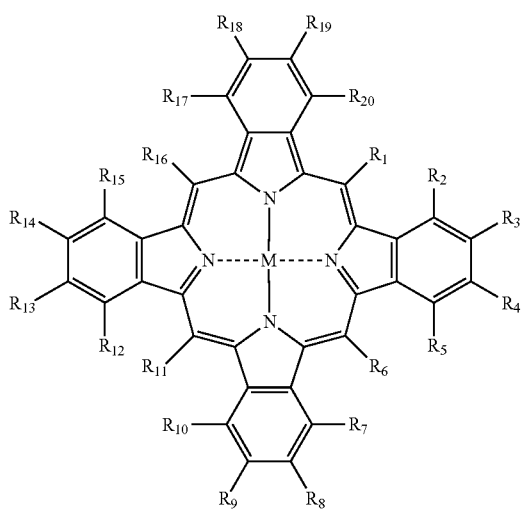

(IV)

wherein:

M is Co, Cu, Fe, Ir, Ni, Pd, Rh, Ru, or Zn;

$R_1$-$R_{20}$ are individually H, $NO_2$, $NH_2$, an amine, $CO_2H$, an ester, a $C_1$-$C_{10}$ alkyl, an ether, SH, or a thioether;

(V)

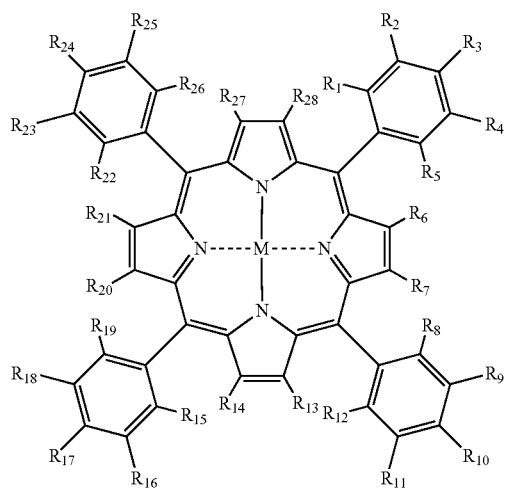

wherein:

M is Co, Cu, Fe, Ir, Ni, Pd, Rh, Ru, or Zn;

$R_1$-$R_{28}$ are individually H, $NO_2$, $NH_2$, an amine, $CO_2H$, an ester, a $C_1$-$C_{10}$ alkyl, an ether, SH, or a thioether; and (VI)

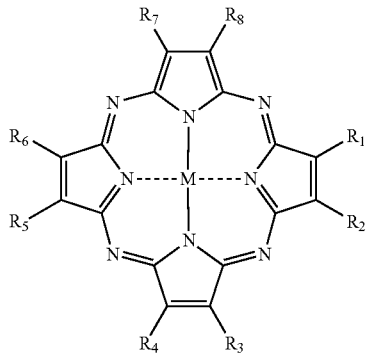

wherein:

M is Co, Cu, Fe, Ir, Ni, Pd, Rh, Ru, or Zn;

$R_1$-$R_8$ are individually H, $NO_2$, $NH_2$, an amine, $CO_2H$, an ester, a $C_1$-$C_{10}$ alkyl, an ether, SH, or a thioether.

17. The electrochemical carbon monoxide sensor of claim 1, wherein the carbonaceous material comprises graphene, graphite, amorphous carbon, carbon nanotubes, carbon fibers, or a combination of any two or more thereof.

18. The electrochemical carbon monoxide sensor of claim 1 further comprising a desiccant for retaining a liquid.

* * * * *